United States Patent [19]
Takano et al.

[11] Patent Number: 5,656,569
[45] Date of Patent: Aug. 12, 1997

[54] THERMAL RECORDING MATERIAL

[75] Inventors: Toshiyuki Takano; Hideki Hayasaka; Yukiko Uehori; Toshimi Satake, all of Tokyo, Japan

[73] Assignee: Nippon Paper Industries Co., Ltd., Tokyo, Japan

[21] Appl. No.: 493,465

[22] Filed: Jun. 22, 1995

[30] Foreign Application Priority Data

Jun. 23, 1994 [JP] Japan .................................. 6-141310

[51] Int. Cl.$^6$ .................................................. B41M 5/30
[52] U.S. Cl. ........................................... 503/216; 503/225
[58] Field of Search ........................... 427/150; 503/216, 503/225, 226

[56] References Cited

U.S. PATENT DOCUMENTS 4,599,630  7/1986  Ohtaki et al. ............................ 346/204

*Primary Examiner*—Bruce H. Hess
*Attorney, Agent, or Firm*—Sherman and Shalloway

[57] ABSTRACT

In a thermal recording material having a thermal recording layer containing a colorless or pale colored dye precursor and a color developer reactable with the dye precursor upon heating to develop a color of the dye precursor, the color developer is a bisurea compound, for example, Compound A-2. The thermal recording material is superior in stability of background color.

5 Claims, No Drawings

THERMAL RECORDING MATERIAL

FIELD OF THE INVENTION

This invention relates to a thermal recording material which is superior in stability of the background color (unrecorded portion).

BACKGROUND OF THE INVENTION

In general, a thermal recording material is obtained by mixing a normally colorless or pale colored electron donating colorless dye and a phenolic compound, each dispersed to fine particles, adding a binder, a filler, a sensitizer, a slip agent, and other additives to form a coating color, and coating the coating color on a substrate such as paper, synthetic paper, films, or plastics, which develops a color by a momentary chemical reaction caused by heating with a thermal head, a hot stamp, or laser light to obtain a visible recording.

Thermal recording material is applied in a wide variety of areas such as measuring recorders, terminal printers for computers, facsimiles, and bar code labels. However, with recent diversification of recording devices for thermal recording materials and advance towards higher performance, quality requirements for thermal recording material have become higher and more difficult to achieve. For example, for high-speed recording, a thermal recording material which can provide a high recording density even with a small thermal energy is in demand. On the other hand, in view of storage stability of recording material, a thermal recording material is required which is superior in light resistance, oil resistance, water resistance, and solvent resistance.

Further, with the popularization of plain paper recording system such as electrophotographic or ink-jet systems, the thermal recording system has become often compared with these plain paper recording systems. For this reason, for example, stability of recorded portion (image) of the thermal recording material, or stability of unrecorded portion (background portion or white portion) before and after recording are required to be closer in quality to those of plain paper recording. Above all, the thermal recording material is required to have background color stabilities for heat, and for solvent (hereinafter referred respectively to as background color heat resistance, and background color solvent resistance). In other words, the recording material is required to have a "thermal sensitivity" only during recording, and a "thermal insensitivity" in other than recording.

As to the background color stability of thermal recording material, for example, Japanese Patent Laid-open Publication (OPI) 04-353490 discloses a thermal recording material having a relatively good background color stability even at a high temperature of about 90° C. This thermal recording material contains 4-hydroxydiphenylsulfone compound and a metal salt of phosphate.

The background color stability of the thermal recording material disclosed in Japanese OPI 04-353490 is a Macbeth density of background color of about 0.11 when treated in a dryer at 95° C. for 5 hours, which is fairly good, however, it has been still insufficient for stability at higher temperatures, for example, 150° C.

Therefore, an object of the present invention is to provide a thermal recording material which is superior in background color stability.

SUMMARY OF THE INVENTION

The above object has been intended to be solved by a thermal recording material using a bisurea compound having a phenolic hydroxyl group as a color developer.

Japanese OPIs 53-140043, 57-87993, 57-82787, and 59-67083 disclose thermal recording materials which use a urea compound and phenol-based color developers (bisphenol A, bisphenol S, and the like which have been known in the art as color developers). In these patents, the urea compound is limited only in terms of the number of carbon atoms, and is thus basically used merely as a melting point controller of the phenol-based color developers. However, the thermal recording materials using a urea compound in combination with phenol-based color developers do not have a sufficient background color thermal resistance.

Further, patents using a specific monourea compound in thermal recording materials are disclosed in Japanese OPIs 58-211496, 59-184694, and 61-21185. The monourea compound used in these patents is a urea compound of which only one amino group of urea is substituted. However, the thermal recording materials using the urea compound alone as a color developer have not exhibited a sufficient background color thermal resistance. Also in these patents, phenol-based color developers are used in combination, and a good background color thermal resistance could not obtained with such a combination.

Still further, thermal recording materials using a bisurea compound are disclosed in Japanese OPIs 05-1317152 and 05-147357. This bisurea compound is characterized in that the sulfonyl group has two units of a certain structure (Ar—SO$_2$—NH—C(=O)—NH—) adjacent to the urea group. However, even with these urea compounds, thermal resistance at high temperatures over 120° C. has been insufficient.

The inventors have found that a thermal recording material which is superior in background color stability can be obtained by using a specific bisurea compound (bisurea compound having a phenolic hydroxyl group) as a color developer, and accomplished the present invention.

Specifically, the present invention provides a thermal recording material having a thermal recording layer containing a colorless or pale colored dye precursor and a color developer which is reactable with the dye precursor upon heating to develop a color of the dye precursor, characterized in that the color developer is a bisurea compound of Formula (1), and the thermal recording layer contains at least one of the bisurea compound.

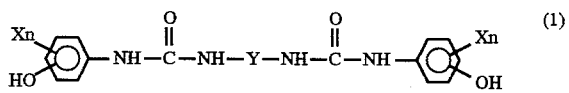

(wherein X denotes an alkyl group of 1 to 12 carbon atoms, a halogenated alkyl group of 1 to 6 carbon atoms, an alkoxy group of 1 to 6 carbon atoms, nitro group, halogen atom, or hydrogen atom; Y denotes a divalent group of within 30 carbon atoms; n is an integer of 1 or 2.).

The bisurea compound of Formula (1) used in the present invention includes bisurea compounds wherein two hydroxyarylureido structures (HO—Ar—NH—C(=O)—NH—) are joined by a joint group. For example, the bisurea compounds are broadly classified by the joint group into the following.

1) Bisurea compounds wherein the joint group is a straight-chain alkylene group of 1 to 12 carbon atoms (methylene, ethylene, n-propylene, n-butylene, n-pentamethylene, n-hexamethylene, n-heptamethylene, n-octamethylene, n-nonamethylene, n-decamethylene, n-undecamethylene, or n-dodecamethylene).

2) Bisurea compounds wherein the joint group is an alkylene group having a branched chain of 1 to 15 carbon atoms.

3) Bisurea compounds wherein the joint group is a straight-chain alkylene group of 1 to 12 carbon atoms containing nitrogen atom or oxygen atom in the straight chain.

4) Bisurea compounds wherein the joint group has 3 to 20 carbon atoms and contains at least one substituted or unsubstituted cycloalkyl ring.

More specifically, these bisurea compounds can further be divided into those in which the two hydroxyarylureido structures are linked directly to one cycloalkyl ring (e.g. cyclohexyl ring), those in which the two hydroxyarylureido structures are linked to dicycloalkyl (e.g. dicyclohexylmethane, dicyclohexylethane), those in which the two hydroxyarylureido structures are linked to the alkyl group portion of dialkylcycloalkyl, and the like.

5) Bisurea compounds wherein the joint group contains a substituted or unsubstituted aromatic ring (e.g. benzene ring, naphthalene ring).

These compounds can further be divided into those in which the two hydroxyarylureido structures are linked directly to a substituted or unsubstituted aromatic ring (e.g. benzene, toluene, xylene, naphthalene), those in which the two hydroxyarylureido structures are linked to the alkyl group portions of two alkyl-substituted aromatic rings, and the like.

6) Bisurea compounds wherein the joint group contains two or more substituted or unsubstituted aromatic rings (e.g. benzene ring, naphthalene ring).

For example, bisurea compounds in which the two hydroxyarylureido structures are linked to a diphenyl compound (e.g. diphenylmethane, diphenylethane, diphenylether, diphenylsulfone, diphenylsulfide, benzophenone).

In addition to the above, those bisurea compounds wherein the joint group has an isophorone ring or a piperazine ring are considered.

The bisurea compound of Formula (1) can readily be synthesized by a reaction of an aniline derivative having phenolic hydroxyl group with a diisocyanate compound (reaction of formula (a)), a reaction of hydroxyaryl isocyanate with diamines (reaction of formula (b)), hydrolysis of a bisurea compound having an alkylcarbonyloxy group or an arylcarbonyloxy group in the terminal arylureido structure (reaction of formula (c)), or the like.

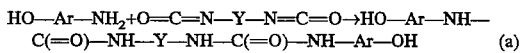

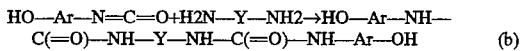

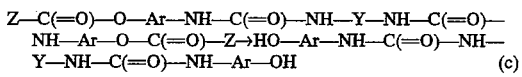

Of these reactions, the reaction of (a) is the most advantageous in view of the availability of starting material and simplicity of the reaction procedure. In the synthesis according to the reaction of (a), the joint group comes from the structure of the diisocyanate compound. Therefore, in selecting the joint group, a joint group originated from diisocyanate compounds described later is advantageous in view of the availability.

In the reaction (a), the aniline derivative having phenolic hydroxyl group includes o-aminophenol, m-aminophenol, p-aminophenol, 2-amino-m-cresol, 2-amino-p-cresol, 3-amino-o-cresol, 3-amino-p-cresol, 4-amino-o-cresol, 4-amino-p-cresol, 5-amino-o-cresol, 6-amino-p-cresol, 3-(1-hydroxyethyl) aniline, 3-hydroxy-4-methoxyaniline, 2-hydroxy-4-methoxyaniline, 2-amino-3-nitrophenol, 2-amino-4-nitrophenol, 2-amino-5-nitrophenol, 4-amino-2-nitrophenol, 4-amino-3-nitrophenol, 2-amino-4-chlorophenol, and the like. On the other hand, the diisocyanate compound includes 2,4-toluenediisocyanate (2,4-TDI), 2,6-toluenediisocyanate (2,6-TDI), 4,4'-diphenylmethanediisocyanate (MDI), 1,5-naphthalenediisocyanate (NDI), tolidinediisocyanate (TODI), hexamethylenediisocyanate (HDI), isophoronediisocyanate (IPDI), p-phenylenediisocyanate, m-phenylenediisocyanate, trans-cyclohexane-1,4-diisocyanate, xylylenediisocyanate (XDI), 4,4'-dicyclohexylmethanediisocyanate (hydrated MDI), lysinediisocyanate (LDI), m-tetramethylxylenediisocyanate (m-TMXDI), p-tetramethylxylenediisocyanate (p-TMXDI), and the like. Any combinations from both groups can be used.

Examples of the bisurea compound of Formula (1) include the following.

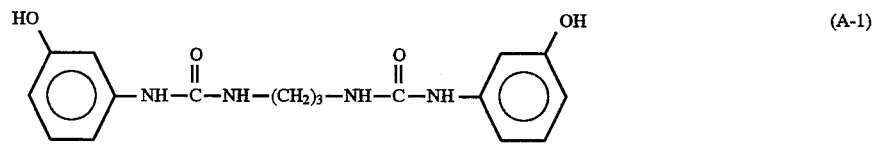

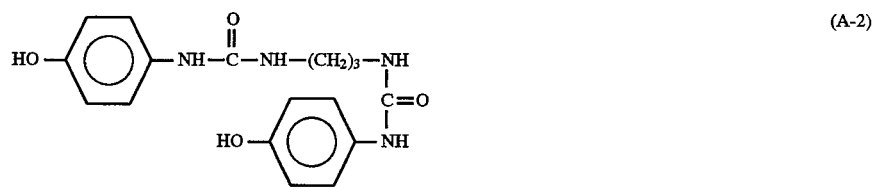

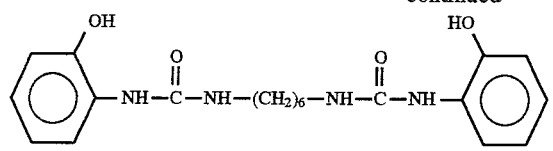
(A-3)
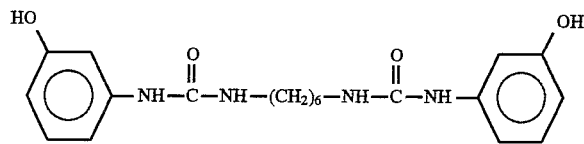
(A-4)
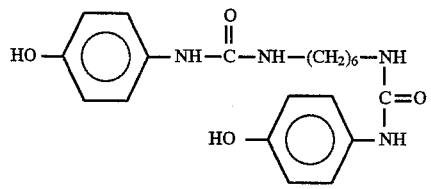
(A-5)
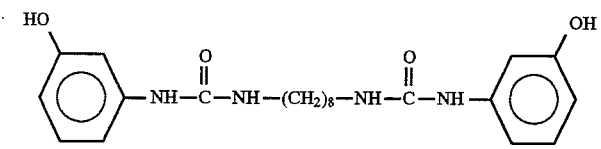
(A-6)
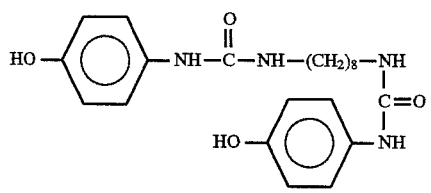
(A-7)
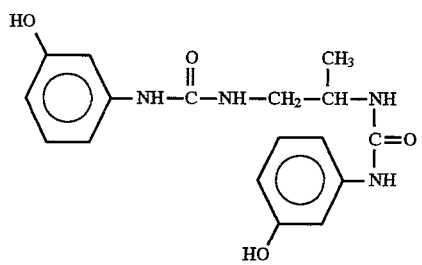
(A-8)
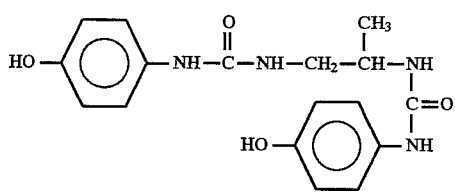
(A-9)
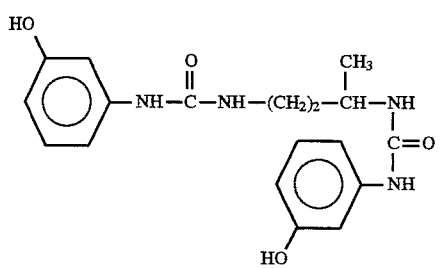
(A-10)

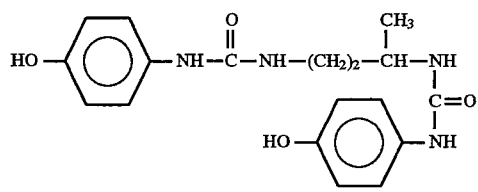 (A-11)
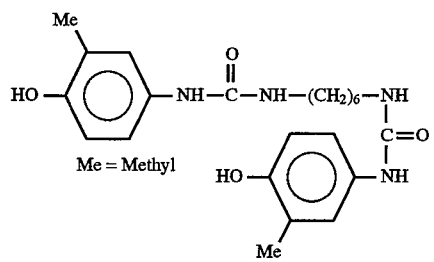 (A-12)
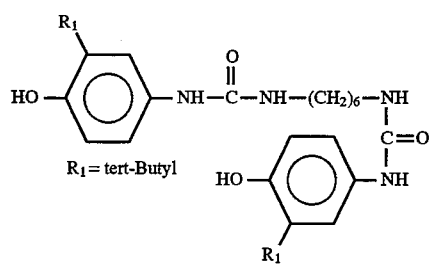 (A-13)
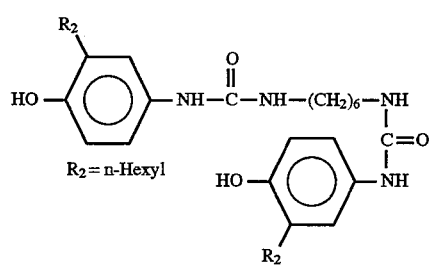 (A-14)
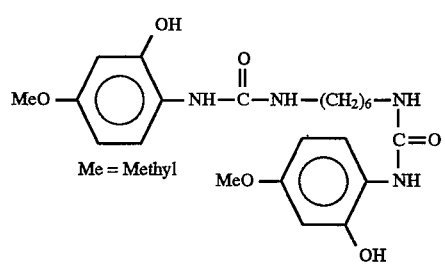 (A-15)
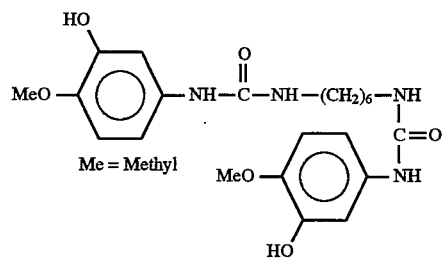 (A-16)

-continued
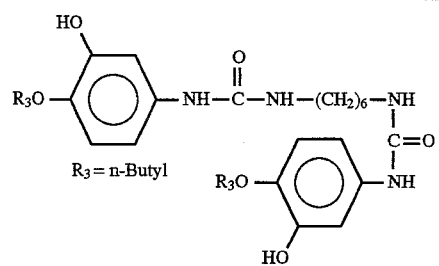
(A-17)
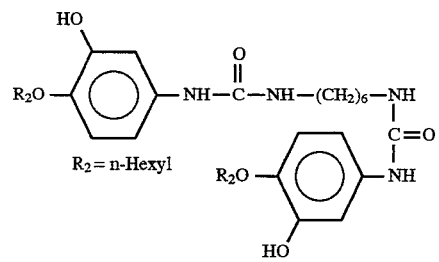
(A-18)
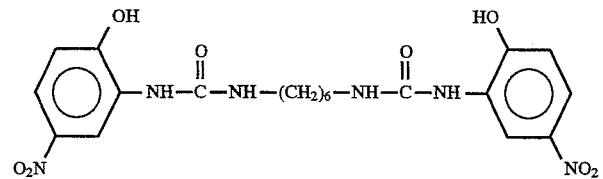
(A-19)
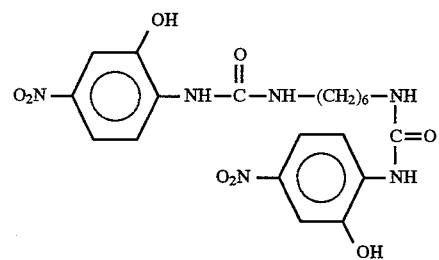
(A-20)
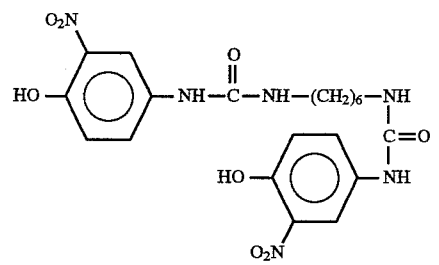
(A-21)
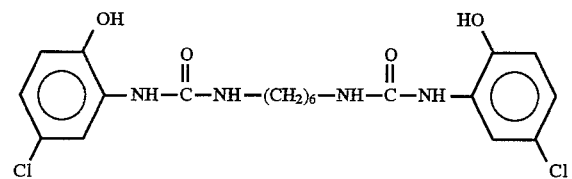
(A-22)

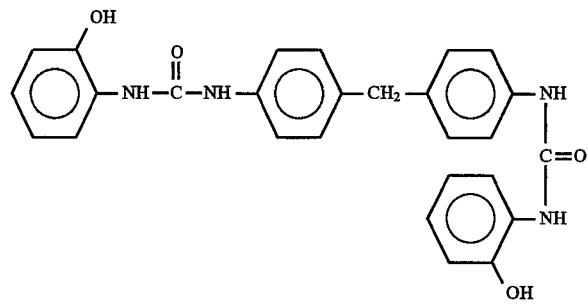
(A-23)
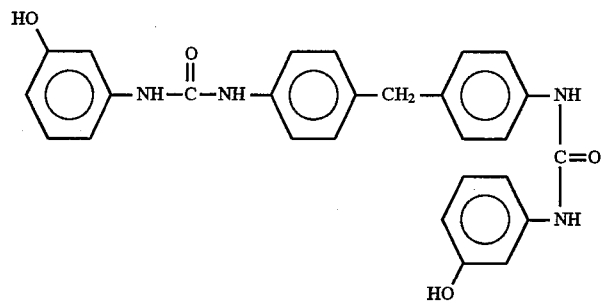
(A-24)
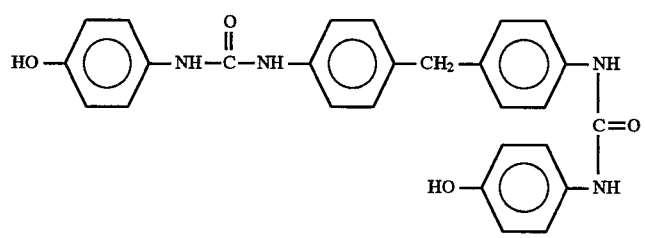
(A-25)
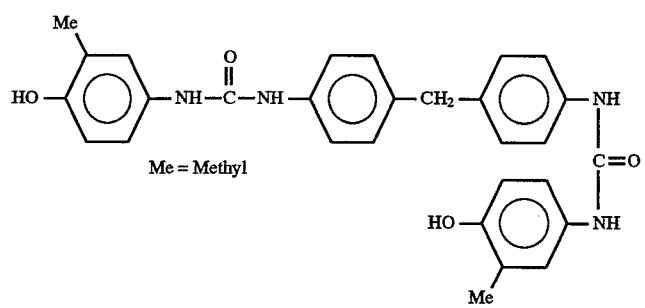
(A-26)
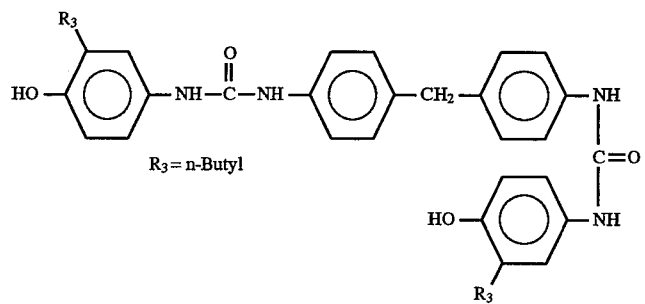
(A-27)

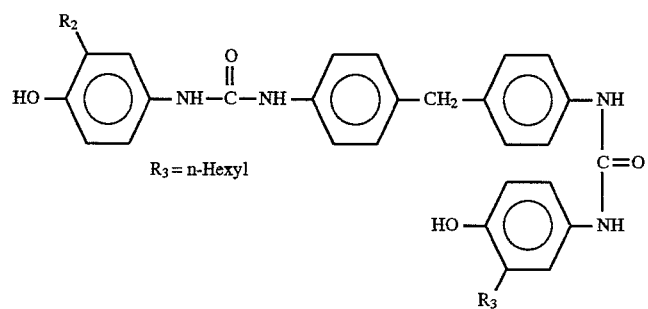
(A-28)
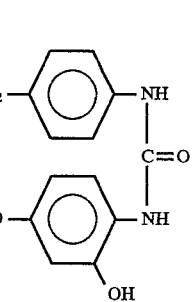
(A-29)
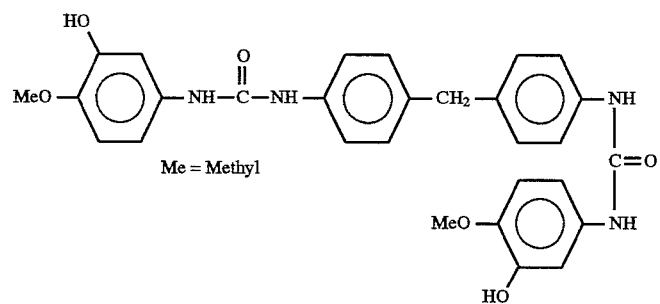
(A-30)
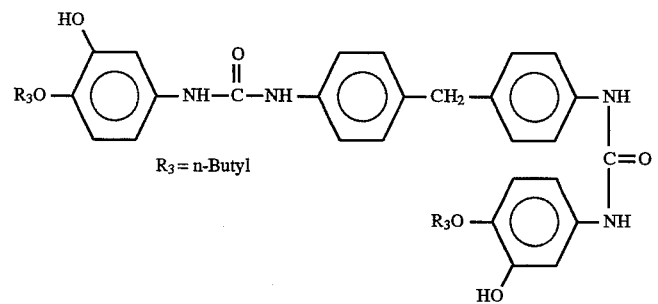
(A-31)
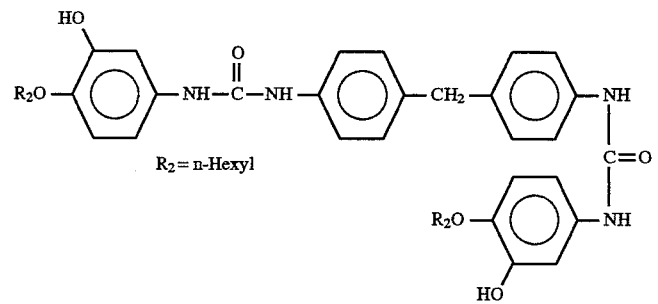
(A-32)

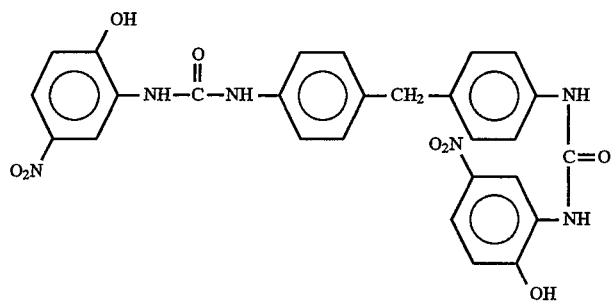
(A-33)
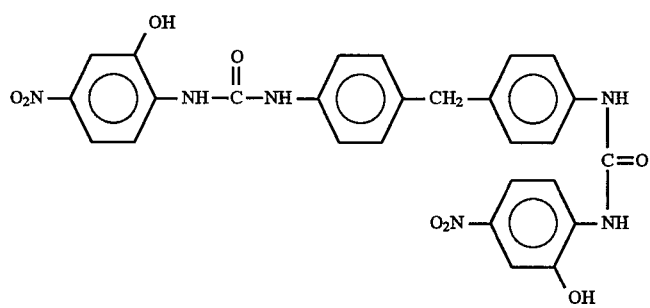
(A-34)
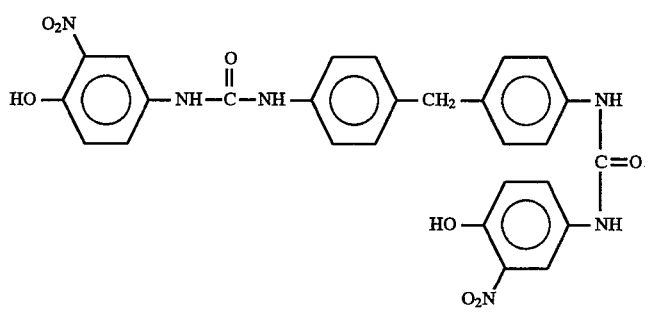
(A-35)
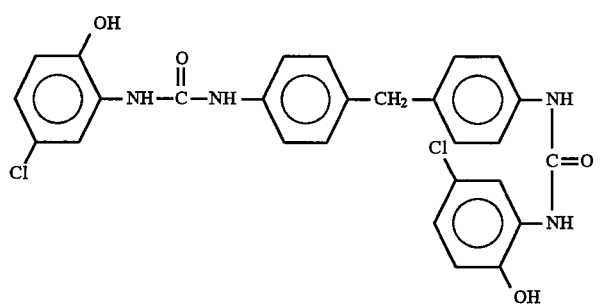
(A-36)
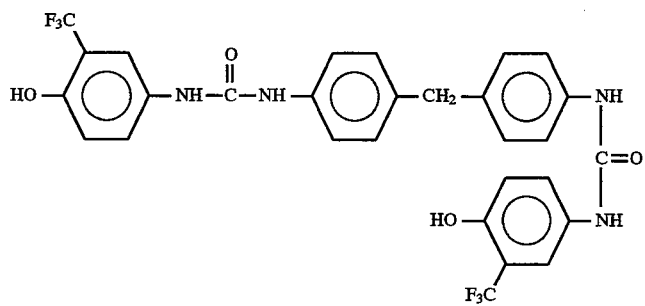
(A-37)

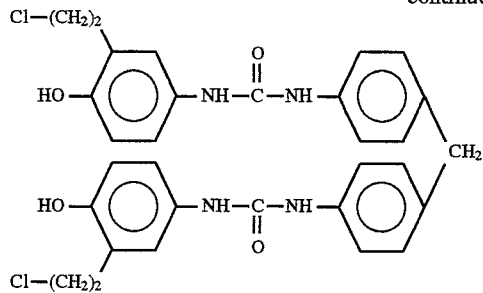
(A-38)
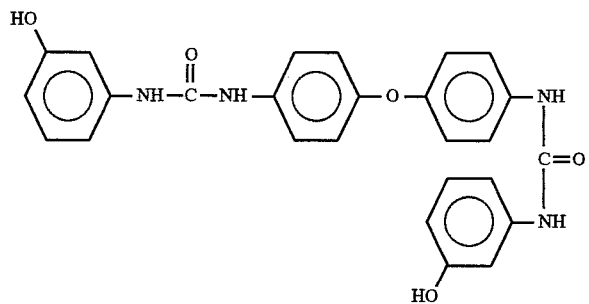
(A-39)
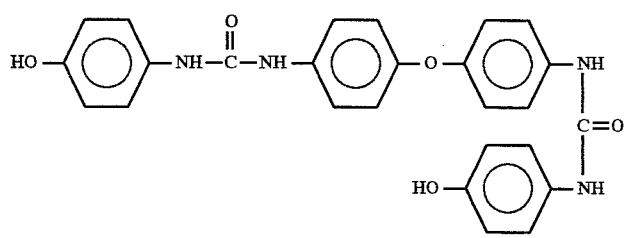
(A-40)
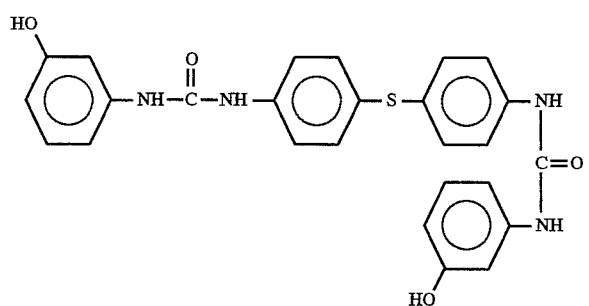
(A-41)
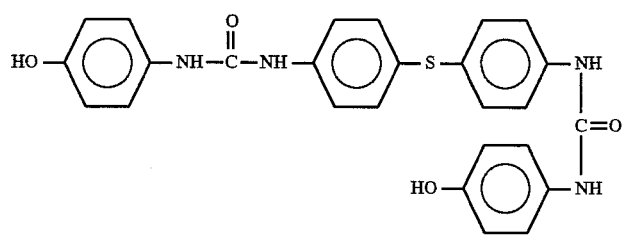
(A-42)
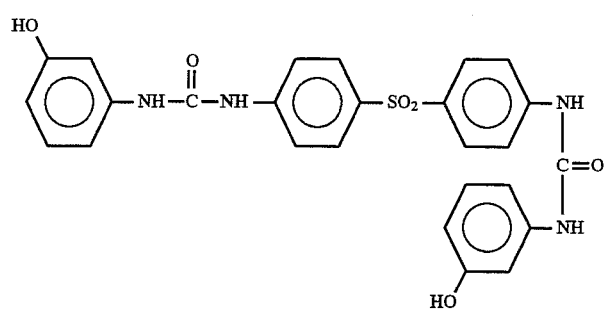
(A-43)

-continued
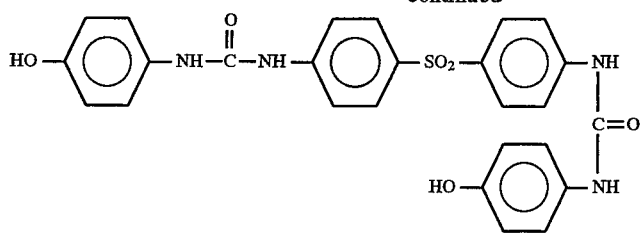 (A-44)
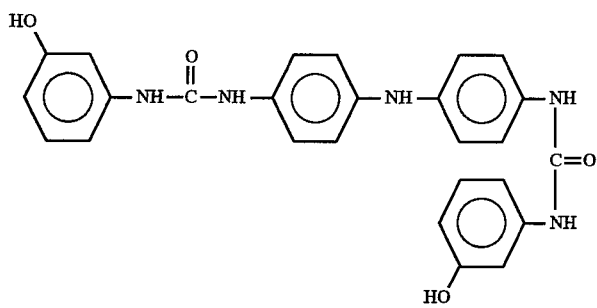 (A-45)
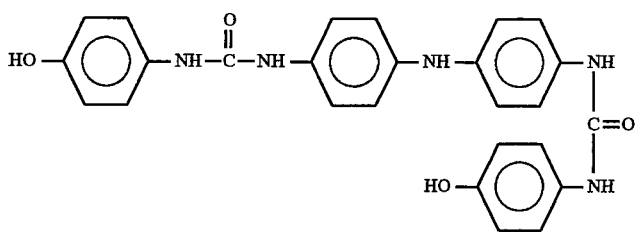 (A-46)
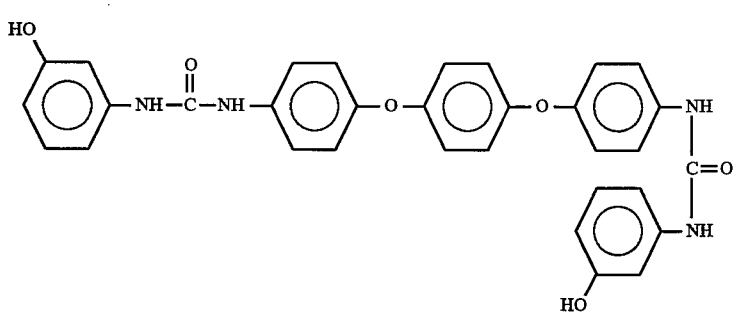 (A-47)
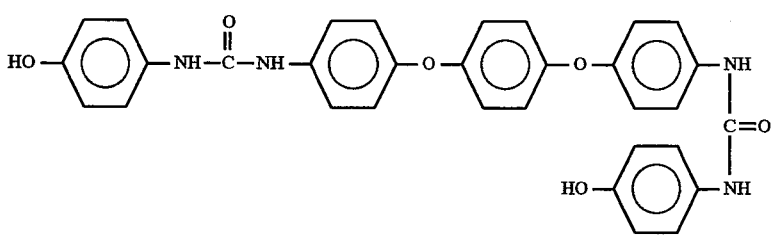 (A-48)
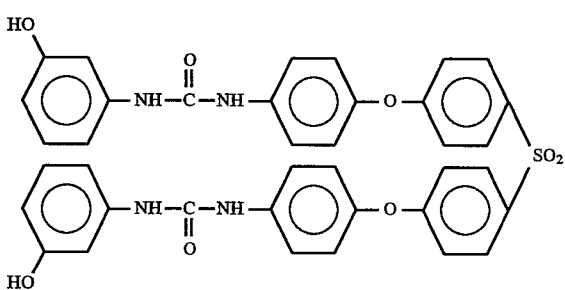 (A-49)

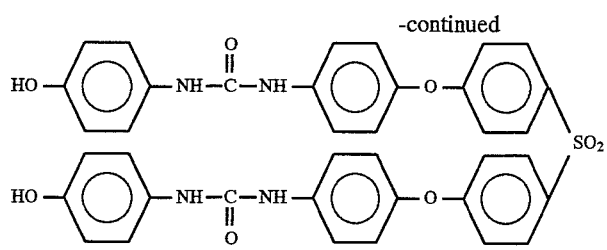
(A-50)
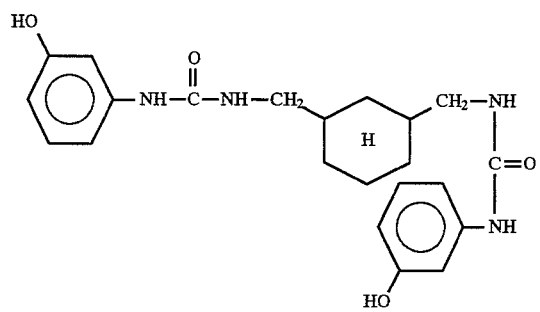
(A-51)
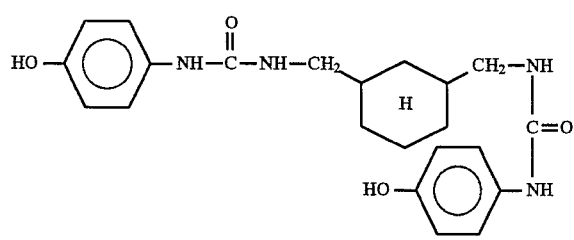
(A-52)
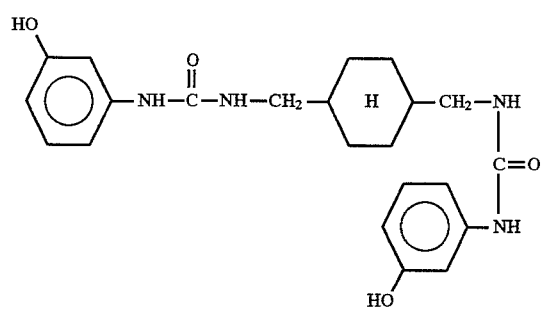
(A-53)
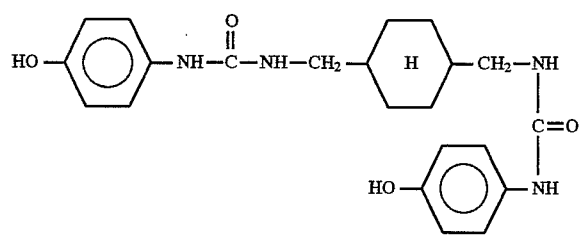
(A-54)
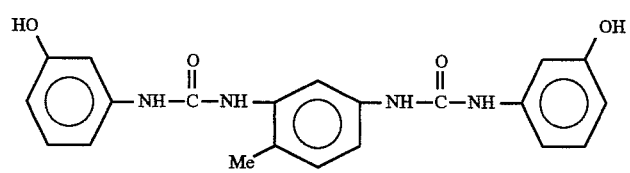
(A-55)
Me = Methyl
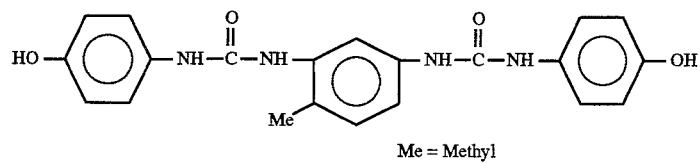
(A-56)
Me = Methyl

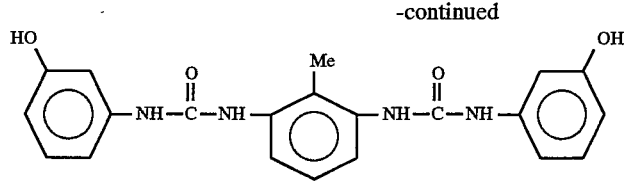
(A-57)
Me = Methyl
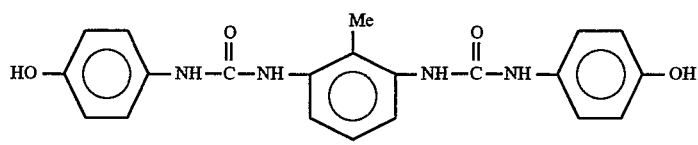
(A-58)
Me = Methyl
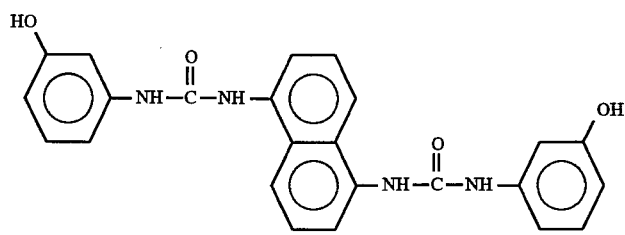
(A-59)
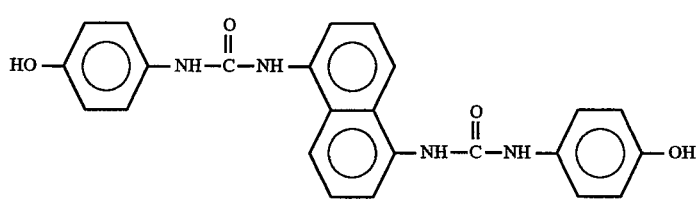
(A-60)
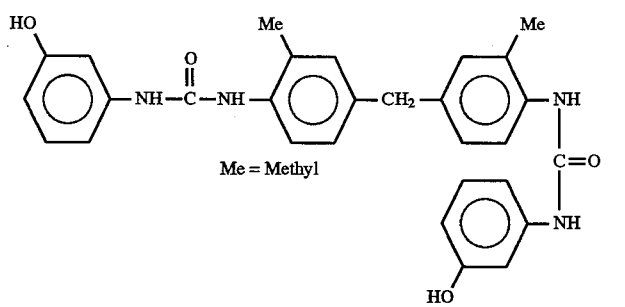
(A-61)
Me = Methyl
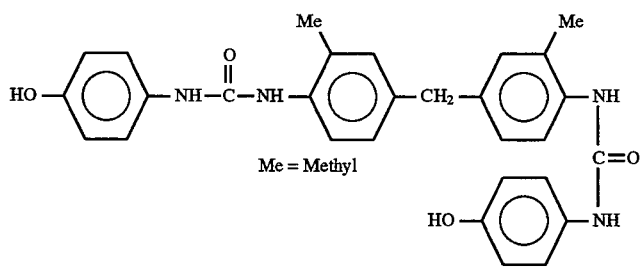
(A-62)
Me = Methyl
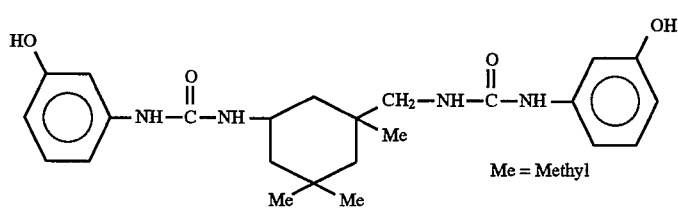
(A-63)
Me = Methyl -continued
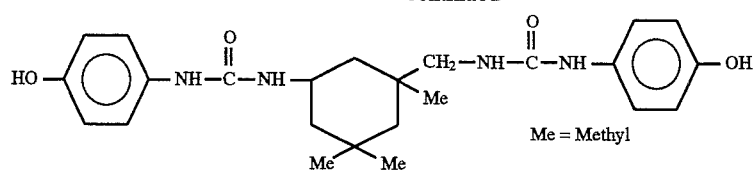
(A-64)
Me = Methyl
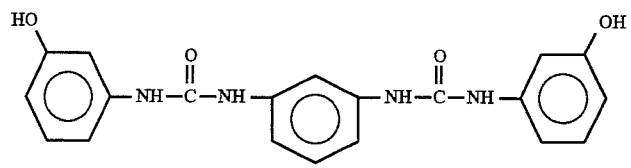
(A-65)
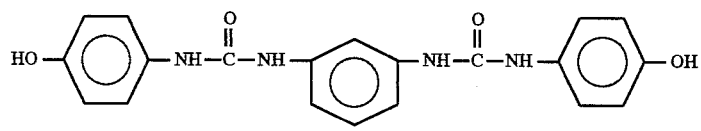
(A-66)
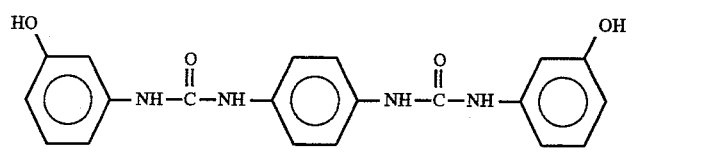
(A-67)
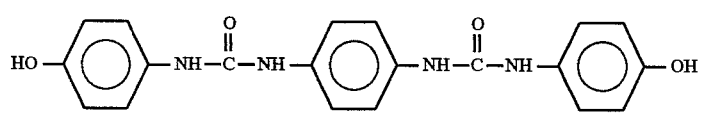
(A-68)
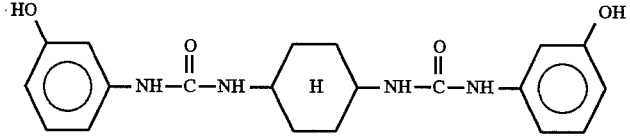
(A-69)
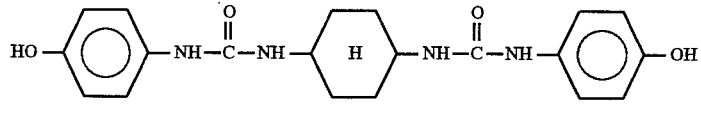
(A-70)
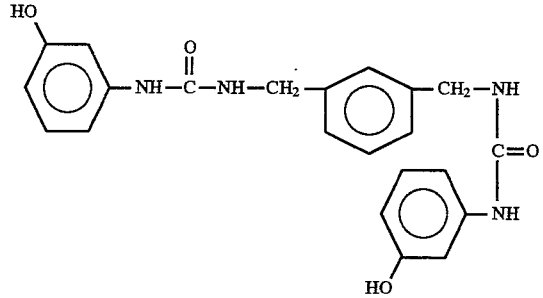
(A-71)
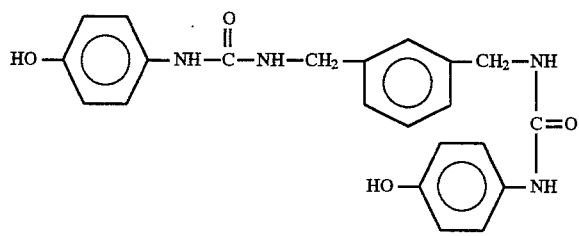
(A-72)

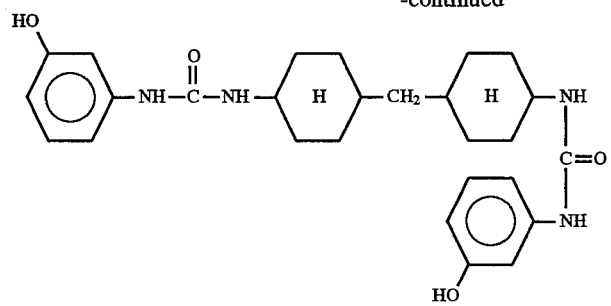
(A-73)
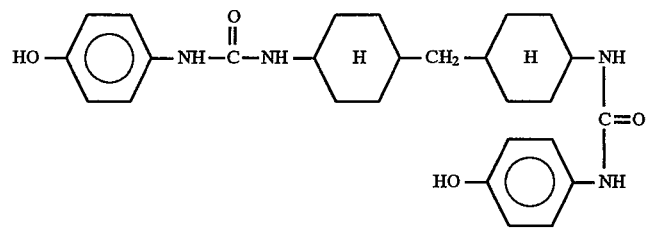
(A-74)
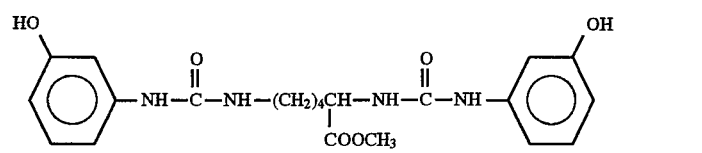
(A-75)
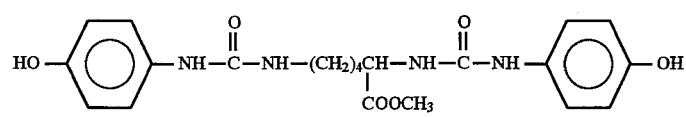
(A-76)
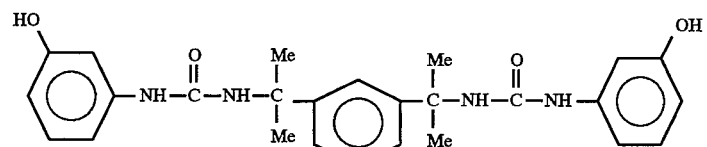
(A-77)
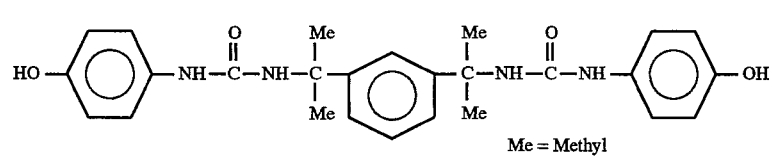
(A-78)
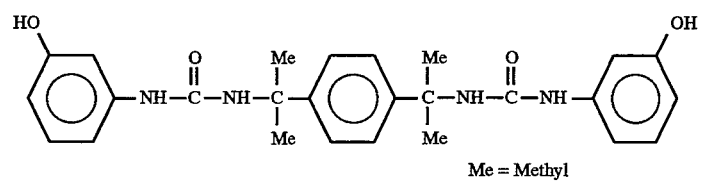
(A-79)
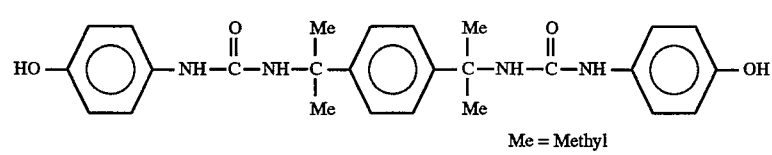
(A-80)
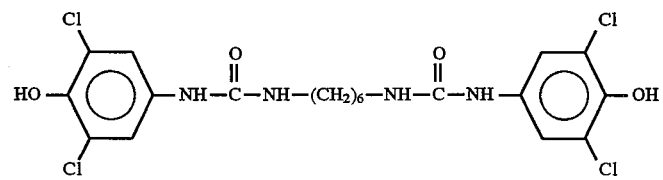
(A-81)

-continued

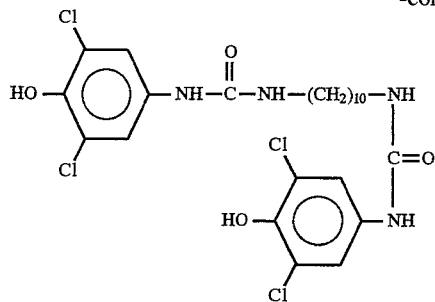
(A-82)

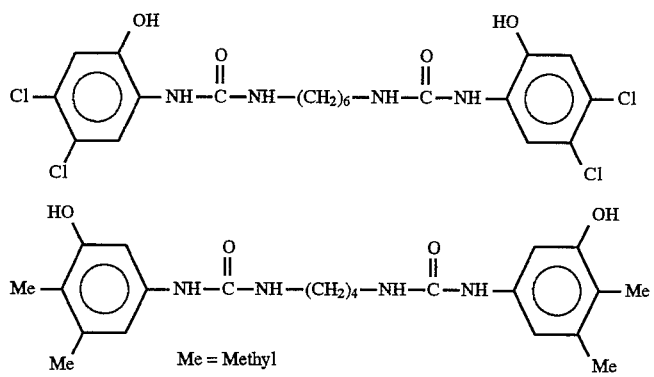
(A-83)

(A-84)

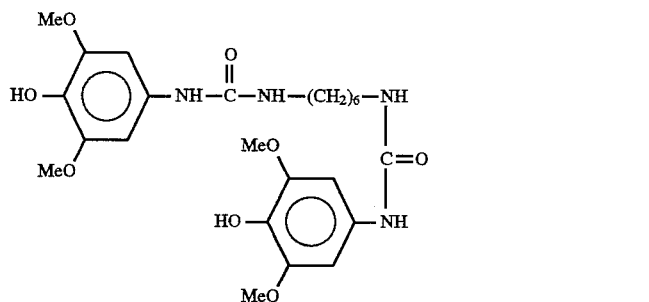

(A-85)

As to the joint group, the joint group (Y) of the bisurea compound of Formula (1) should be selected in consideration of the melting point, decomposition point, and solubility in solvents, and the like of the bisurea compound, properties of the produced thermal recording material (recording density, stability of recorded portion, background color stability, and the like), or readiness of synthesis (availability of starting materials, reaction yield, and the like), but is not specifically limited. However, in view of the recording density, more preferably the joint group is a straight-chain alkylene group of 1 to 12 carbon atoms, or an alkylene group having a branched chain of 1 to 15 carbon atoms.

That is, the thermal recording material preferably has a thermal recording layer containing a colorless or pale colored dye precursor and a color developer reactable with the dye precursor upon heating to develop a color of the dye precursor, characterized in that the color developer is a bisurea compound of Formula (2), and the thermal recording layer contains at least one of the bisurea compound.

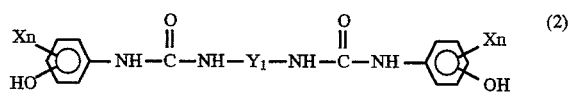 (2)

(wherein X denotes an alkyl group of 1 to 12 carbon atoms, a halogenated alkyl group of 1 to 6 carbon atoms, an alkoxy group of 1 to 6 carbon atoms, nitro group, halogen atom, or hydrogen atom; $Y_1$ denotes a straight-chain alkylene group of 1 to 12 carbon atoms, or an alkylene group having a branched chain of 1 to 15 carbon atoms; n is an integer of 1 or 2.).

Further, considering the availability, for example, a bisurea compound of Formula (3) is more preferable.

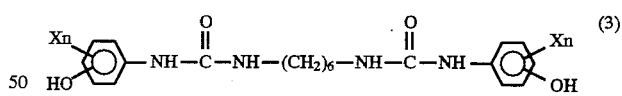 (3)

(wherein X denotes an alkyl group of 1 to 12 carbon atoms, an alkoxy group of 1 to 6 carbon atoms, nitro group, halogen atom, or hydrogen atom. n is an integer of 1 or 2.).

On the other hand, considering the hydroxyarylureido structures at both terminals, the aromatic ring substituent (X) of the hydroxyarylureido structure of the bisurea compound of Formula (1) should be appropriately selected according to the melting point, decomposition point, and solubility in solvents of the bisurea compound, or properties of the produced thermal recording material (recording density, stability of recorded portion, background color stability), and is not specifically limited. However, in view of the recording density, it is more preferable that the aromatic ring substituent (X) is hydrogen atom (that is, unsubstituted), or an electron attracting group (halogenated alkyl group, nitro group, halogen atom), which provides a higher recording density. When the recording density, background color stability, economy (cost), and the like are totally considered, the aromatic ring substituent (X) is the most preferably hydrogen atom which is the best balanced.

Further, as to the hydroxyl group of the hydroxyarylureido structure of the bisurea compound of Formula (1), p-position or m-position is better than o-position of the hydroxyl group to the ureido structure in terms of the background color thermal stability. Further, the p-position is higher in background color thermal stability than the m-position, and is thus the most preferable.

The thermal recording material using the bisurea compound of Formula (1) is superior in the background color stability to heat and solvents. That is, even when the recording material is placed in a high-temperature environment above 120° C., background color of the recording surface (surface having the thermal recording layer) of the thermal recording material is not substantially changed (does not develop a color). However, when the recording material is momentarily applied with a high energy of a thermal head at normally 200° to 300° C., the recording material develops a high-density color. In known thermal recording materials, it could not be considered that, for the thermal resistance of the background color, no color is developed when a heat block at over 120° C. is contacted against the surface of the thermal recording layer, but recording of practicable density is achieved by a thermal head. Such a material has not been known in the past.

Since the thermal recording material of the present invention has a high thermal resistance, it can be subjected to, for example, (a) heat lamination of the recording surface after thermal recording with a plastic film or the like, (b) adherence of a toner onto the thermal recording layer surface as a electrophotographic transfer sheet, or (c) adherence of a toner onto the thermal recording surface of thermally recorded sheet followed by thermal fixing.

The thermal recording material of the present invention has an advantage that the production process control is very easily. That is, heretofore, in the production of thermal recording materials, the drying process after coating the thermal recording layer has required a very strict temperature control so that the background color of the coated surface is not developed. Therefore, high-speed coating has been limited. However, since the thermal recording material of the present invention does not cause development of the background color even when exposed to hot air at 120° C., high-temperature drying in the drying process is possible, and since the control range of the drying temperature can be remarkably increased, a considerable improvement of productivity can be expected.

Further, the thermal recording material of the present invention, since the bisurea compound seam to be low in solubility in organic solvents, does not discolor due to oil-based ink. Therefore, it is possible to write with an oil-based ink on the thermal recording layer surface of the thermal recording material.

Still further, the thermal recording material of the present invention, possibly because the bisurea compound of Formula (1) has a phenolic hydroxyl group, is good in recording sensitivity. For example, the thermal recording material of the present invention is superior to a thermal recording material which uses a urea compound alone having no phenolic hydroxyl group as a color developer.

As described above, the bisurea compound of Formula (1) is a superior thermal recording material in terms of the background color stability (thermal resistance, solvent resistance, and the like).

A general method for producing the thermal recording material of the present invention is that (a) a dye precursor, and (b) a urea compound of Formula (1) as a color developer are dispersed with a binder having a dispersing function, auxiliaries such as a filler and a slip agent are added as necessary to prepare a coating color, which is coated on a substrate and dried by a conventional method known in the art.

In the present invention, the bisurea compound can be used alone or in combination of two or more types. Further, urea compounds described, for example, in Japanese Patent Applications 05-231105, 05-250328, 05-250329, 05-311502, 05-315023, 05-317211, 05-321506, 06-100082, 06-144159, 06-144160, 06-14461, 06-184285, 07-9806, 07-21507 and 07-55506 can be used in combination.

Further, in the thermal recording material of the present invention, it is in principle better not to use a conventional phenol compound, which has been known as a color developer, in combination. When a phenol compound is used, properties of the thermal recording material (recording adaptability, thermal resistance, solvent resistance, and the like) depend mainly on the phenol compound. Therefore, a thermal recording material using a phenol compound cannot provide sufficient thermal resistance of background color and the like. However, a known color developer which develops the color of the dye precursor (e.g. bisphenol A, bisphenol S, benzyl 4-hydroxybenzoate, 4-hydroxy-4'-isopropoxydiphenylsulfone) may be used in combination in a small amount as far as the properties such as background color stability (thermal resistance, solvent resistance, and the like) of the produced thermal recording material are not impaired.

The dye precursor used in the thermal recording material of the present invention may be those which are known in the field of thermal recording, and is not specifically limited, but triphenylmethane-type leuco dyes, fluorane-type leuco dyes, fluorene-type leuco dyes, and the like are preferable. Examples of typical dye precursor are shown below.

3,3-Bis(4'-dimethylaminophenyl)-6-dimethylaminophthalide (Crystal Violet Lactone (CVL))
3,3-Bis(4'-dimethylaminophenyl)-6-pyrrolidylphthalide
3,3-Bis(4'-dimethylaminophenyl)phthalide (Malachite Green Lactone (MGL))
Tris[4-(dimethylamino)phenyl]methane (Leuco Crystal Violet (LCV))
3-Dimethylamino-6-methyl-7-(m-trifluoromethylanilino) fluorane
3-Diethylamino-6-methyl-fluorane
3-Diethylamino-7-methyl-fluorane
3-Diethylamino-7-chlorofluorane
3-Diethylamino-6-methyl-7-chlorofluorane
3-Diethylamino-6-methyl-7-anilinofluorane
3-Diethylamino-6-methyl-7-p-methylanilinofluorane
3-Diethylamino-6-methyl-7-(o,p-dimethylanilino)fluorane
3-Diethylamino-6-methyl-7-(m-trifluoromethylanilino) fluorane
3-Diethylamino-6-methyl-7-(o-chloroanilino)fluorane
3-Diethylamino-6-methyl-7-(p-chloroanilino)fluorane
3-Diethylamino-6-methyl-7-(o-fluoroanilino)fluorane
3-Diethylamino-6-methyl-7-(p-n-butylanilino)fluorane
3-Diethylamino-6-methyl-7-n-octylaminofluorane
3-Diethylamino-6-chloro-7-anilinofluorane
3-Diethylamino-6-ethoxyethyl-7-anilinofluorane
3-Diethylamino-benzo[a]fluorane
3-Diethylamino-benzo[c]fluorane
3-Diethylamino-6-methyl-7-benzylaminofluorane
3-Diethylamino-6-methyl-7-dibenzylaminofluorane
3-Diethylamino-7-di(p-methylbenzyl)aminofluorane
3-Diethylamino-6-methyl-7-diphenylmethylaminofluorane 3-Diethylamino-7-dinaphthaylmethylaminofluorane
10-Diethylamino-4-dimethylaminobenzo[a]fluorane
3-Dibutylamino-7-(o-chloroanilino)fluorane
3-Dibutylamino-6-methylfluorane
3-Dibutylamino-6-methyl-7-chlorofluorane
3-Dibutylamino-6-methyl-7-anilinofluorane
3-Dibutylamino-6-methyl-7-p-methylanilinofluorane
3-Dibutylamino-6-methyl-7-(o,p-dimethylanilino)fluorane
3-Dibutylamino-6-methyl-7-(m-trifluoromethylanilino)fluorane
3-Dibutylamino-6-methyl-7-(o-chloroanilino)fluorane
3-Dibutylamino-6-methyl-7-(p-chloroanilino)fluorane
3-Dibutylamino-6-methyl-7-(o-fluoroanilino)fluorane
3-Dibutylamino-6-methyl-7-(p-n-butylanilino)fluorane
3-Dibutylamino-6-methyl-7-n-octylaminofluorane
3-Dibutylamino-6-chloro-7-anilinofluorane
3-Dibutylamino-6-ethoxyethyl-7-anilinofluorane
3-Di-n-pentylamino-6-methyl-7-anilinofluorane
3-Di-n-pentylamino-6-methyl-7-(o,p-dimethylanilino)fluorane
3-Di-n-pentylamino-6-methyl-7-(m-trifluoromethylanilino)fluorane
3-Di-n-pentylamino-6-methyl-7-(o-chloroanilino)fluorane
3-Di-n-pentylamino-6-methyl-7-(p-chloroanilino)fluorane
3-Di-n-pentylamino-6-methyl-7-(o-fluoroanilino)fluorane
3-Pyrrolidino-6-methyl-7-anilinofluorane
3-Piperidino-6-methyl-7-anilinofluorane
3-(N-methyl-N-n-propylamino)-6-methyl-7-anilinofluorane
3-(N-ethyl-N-n-propylamino)-6-methyl-7-anilinofluorane
3-(N-ethyl-N-isopropylamino)-6-methyl-7-anilinofluorane
3-(N-ethyl-N-n-butylamino)-6-methyl-7-anilinofluorane
3-(N-ethyl-N-isobutylamino)-6-methyl-7-anilinofluorane
3-(N-ethyl-N-n-hexylamino)-6-methyl-7-p-methylanilinofluorane
3-(N-ethyl-N-n-hexylamino)-6-methyl-7-(o,p-dimethylanilino)fluorane
3-(N-ethyl-N-n-hexylamino)-6-methyl-7-(m-trifluoromethylanilino)fluorane
3-(N-ethyl-N-n-hexylamino)-6-methyl-7-(o-chloroanilino)fluorane
3-(N-ethyl-N-isoamylamino)-6-methyl-7-anilinofluorane
3-(N-ethyl-N-isoamylamino)-6-chloro-7-anilinofluorane
3-(N-ethyl-N-3-methylbutylamino)-6-methyl-7-anilinofluorane
3-(N-ethyl-N-p-toluidino)-6-methyl-7-anilinofluorane
3-(N-ethyl-N-p-toluidino)-6-methyl-7-(p-methylanilino)fluorane
3-(N-ethyl-N-p-toluidino)-6-methyl-7-(o,p-dimethylanilino)fluorane
3-(N-ethyl-N-tetrahydrofurfurylamino)-6-methyl-7-anilinofluorane
3-(N-cyclohexyl-N-methylamino)-6-methyl-7-anilinofluorane
3-(N-cyclohexyl-N-methylamino)-7-anilinofluorane
3-(N-ethyl-N-3-methoxypropylamino)-6-methyl-7-anilinofluorane
3-(N-ethyl-N-3-ethoxypropylamino)-6-methyl-7-anilinofluorane
2-(4-Oxahexyl)-3-dimethylamino-6-methyl-7-anilinofluorane
2-(4-Oxahexyl)-3-diethylamino-6-methyl-7-anilinofluorane
2-(4-Oxahexyl)-3-dipropylamino-6-methyl-7-anilinofluorane
3-(4"-Aminostilbuldyl-4'-amino)-7,8-benzofuran
3,6,6'-Tris(dimethylamino)spiro[fluorene-9,3'-phthalide]
3,6,6'-Tris(diethylamino)spiro[fluorene-9,3'-phthalide]
3-(4-Diethylamino-2-ethoxyphenyl)-3-(1-ethyl-2-methylindol-3-yl)-4-azaphthalide
3-(4-Diethylamino-2-ethoxyphenyl)-3-(1-octyl-2-methylindol-3-yl)-4-azaphthalide
3-(4-Diethylamino-2-n-hexylphenyl)-3-(1-ethyl-2-methylindol-3-yl)-4-azaphthalide
3-(4-Cyclohexylmethylamino-2-methoxyphenyl)-3-(1-ethyl-2-methylindol-3-yl)-4-azaphthalide
3-(4-Cyclohexylethylamino-2-methoxyphenyl)-3-(1-ethyl-2-methylindol-3-yl)-4-azaphthalide
3,3-Bis(1-ethyl-2-methylindol-3-yl)phthalide
3,3-Bis(1-methyl-2-octylindol-3-yl)phthalide
3-(1-Ethyl-2-methylindol-3-yl)-3-(1-n-butyl-2-methylindol-3-yl)phthalide
3,7-Bis(dimethylamino)-10-benzoylphenothiazine
3,7-Bis(dimethylamino)-N-[p-N-bis(4,4'-dimethylaminophenyl)methylamino]benzoylphenothiazine
3,7-Bis(dimethylamino)-N-[p-N-bis(4,4'-diethylaminophenyl)methyl]benzoylphenothiazine
3,6-Bis(diethylamino)fluorane-γ-(2'-nitro)anilinolactam
3,6-Bis(diethylamino)fluorane-γ-(3'-nitro)anilinolactam
3,6-Bis(diethylamino)fluorane-γ-(4'-nitro)anilinolactam
3,6-Bis(diethylamino)fluorane-γ-anilinolactam.

These dye precursors may be used alone or as mixtures of two or more types. Of these dye precursors, the fluorane type dye precursors are preferably used in the present invention. Naturally, when thermal stability is particularly important, a dye precursor which is high in melting point and decomposition temperature is preferable.

In the thermal recording material of the present invention, when the background color thermal stability is particularly required, it is better in principle not to use a sensitizer. When a sensitizer is used, the color development temperature depends upon the melting point of the sensitizer. However, depending on the properties required for the produced thermal recording material, sensitizers may be used alone or in combination. Sensitizers used for this purpose include 2-di(3-methylphenoxy)ethane, p-benzylbiphenyl, β-benzyloxynaphthalene, phenyl 1-hydroxy-2-naphthoate, dibenzyl terephthalate, benzyl p-benzyloxybenzoate, diphenylcarbonate, ditolylcarbonate, 4-biphenyl-p-tolylether, m-terphenyl, 1,2-diphenoxyethane, 1,2-bis(m-tolyloxy)ethane, 1,5-bis(p-methoxyphenoxy)-3-oxapentane, dibenzyloxalate, di(p-methylbenzyl)oxalate, and di(p-chlorobenzyl)oxalate.

The binder usable in the present invention includes polyvinylalcohols such as completely-hydrolyzed polyvinylalcohol having a polymerization degree of 200 to 1900, partially-hydrolyzed polyvinylalcohol, carboxy-modified polyvinylalcohol, amide-modified polyvinylalcohol, sulfonic acid-modified polyvinylalcohol, butyral-modified polyvinylalcohol, and other modified polyvinylalcohols; cellulose derivatives such as hydroxyethylcellulose, methylcellulose, carboxymethylcellulose, ethylcellulose, and acetylcellulose; synthetic polymers such as styrene-maleic anhydride copolymer, styrene-butadiene copolymer, polyvinylchloride, polyvinylacetate, polyacrylamide, polyacrylic acid esters, polyvinylbutyral, polystyrene and copolymers thereof; resins such as polyamide resins, silicone resins, petroleum resins, terpene resins, ketone resins, and coumarone resins. Of these binders, the polyvinylalcohol type binder is preferable in terms of the dispersibility, binding properties, and thermal stability of background color. These binders are used by dissolving in solvents such as water, alcohol, ketone, ester, and hydrocarbon, emulsifying in water or other solvents, or dispersing to a paste form, and can be used in combination according to the quality requirements.

The filler used in the present invention includes inorganic fillers such as silica, calcium carbonate, kaolin, calcined kaolin, diatomaceous earth, talc, zinc oxide, titanium oxide, zinc hydroxide, and aluminum hydroxide; polystyrene-based organic fillers, styrene/butadiene-based organic fillers, styrene/acrylic-based organic fillers, and hollow organic fillers.

In addition to the above, a release agent such as fatty acid metal salts, a slip agent such as waxes, benzophenoe or benzotriazole type ultraviolet absorbents, a water-resistant agent such as glyoxal, a dispersant, a defoamer, and the like can be used.

Types and ratios the dye precursor, the bisurea compound of Formula (1), and other ingredients are determined according to the required properties and recording adaptability, and are not specifically limited but, normally, based on one part of the dye precursor, 1 to 8 parts of the bisurea compound, and 1 to 20 parts of the filler are used, and the binder is used in an amount of 10 to 25 % by weight to the total solid. These materials are finely crushed by a crusher such as a ball mill, an attriter, or a sand grinder, or an appropriate emulsifying apparatus to a particle diameter of several microns or less, a binder and, as necessary, other additives are added to obtain a coating color. The coating color is coated on a substrate to obtain the objective thermal recording material.

The substrate used in the present invention includes paper, synthetic paper, non-woven fabrics, metal foils, plastic films, plastic sheets, or composite sheets thereof.

Further, an overcoating layer comprising a polymer can be provided on top of the recording layer to enhance the preservability of the thermal recording material of the present invention, or an undercoating layer of a polymer containing a filler can be provided under the recording layer to enhance the color developing sensitivity.

The thermal recording material of the present invention, utilizing its high background color stability, may be heat laminated with a plastic film to form a transparent and strong protective coating. For example, even after thermal recording, a heat-resistant card can be easily prepared using a commercial simple laminator. The plastic film used in the thermal recording material of the present invention can be thermoplastic resins such as low-density polyethylene, ethylene/vinyl acetate copolymer, ethylene/ethyl acrylate copolymer, ethylene/methyl methacrylate copolymer, and ethylene/methacrylic acid copolymer.

The thermal recording material of the present invention may contain an optical absorbent which absorbs light into the thermal recording layer to convert it to heat. The optical absorbent can be a substance which absorbs wavelengths of various light sources, and is not specifically limited.

For example, for a recording light source having continuous wavelength, such as a stroboflash, the optical absorbent can be a heat reaction product of thiourea derivative/copper compound described in Japanese OPI 02-208583 and Japanese Patent Application 05-30954, graphite, copper sulfide, lead sulfide, molybdenum trisulfide, black titanium, and the like described in Japanese OPI 03-88580, or carbon black.

On the other hand, when a semiconductor laser is used as a recording light source, the optical absorbent can be polymethine type dyes (cyanine dyes), azolenium type dyes, pylylium type dyes, thiopylylium type dyes, squalylium type dyes, chroconium type dyes, dithiol complexes, mercaptophenol-metal complex type dyes, mercaptonaphthol-metal complex type dyes, phthalocyanine type dyes, naphthalocyanine type dyes, triarylmethane type dyes, immonium type dyes, diimmonium type dyes, naphthoquinone type dyes, anthraquinone type dyes, and metal complex type dyes, which are disclosed in Japanese OPIs 54-4142, 58-94494, 58-209594, 02-217287, and 03-73814, Further, the optical absorbents listed for a light source having continuous wavelength can also be used as well.

Specifically, for example, near-infrared absorbent dyes described in Table 1 of Color Chemical Handbook (Organic Synthesis Association, CMC Publishing (1988) p196–200), Table 3 of Kagaku Kogyo (vol. 5, 1986, p379–389), Japanese OPIs 61-69991 and 61-246391, U.S. Pat. Nos. 3,557, 0122, 3,575,871, and 3,637,769, 1,1,5,5-tetrakis(p-dimethylminophenyl)-3-methoxy-1,4-pentadiene (or its cationic form), 1,1,5,5-tetrakis(p-diethylaminophenyl)-3-methoxy-1,4-pentadiene (or its cationic form), toluenedithiolnickel complex, 4-tert-butyl-1,2-benzenedithiolnickel complex, bisdithiobenzylnickel complex, bis(4-ethyldithiobenzyl) nickel complex, bis(4-n-propyldithiobenzyl)nickel complex, and the like can be used. These optical absorbents can be used alone or as mixtures of two or more types.

These optical absorbents may be used by: (a) a method in which the optical absorbent is simply mixed in the materials necessary for the thermal recording material, (b) a method in which the optical absorbent is previously melted and mixed, and dissolved or dispersed in the material necessary for the thermal recording material, as described in Japanese OPI 02-217287, or (c) a method in which the optical absorbent is previously dissolved or dispersed by a solvent in the materials necessary for the thermal recording material, the solvent is removed from the mixture, and then used. The optical absorbent may also be co-dispersed with the color developer, dye precursor, sensitizer, a mixture of the color developer and the sensitizer, or a mixture of the dye precursor and the sensitizer.

The thermal recording material of the present invention, even when combined with the optical absorbent, is substantially unchanged in the background color stability (thermal resistance and solvent resistance). Even a thermal recording material containing an optical absorbent can be heat laminated or toner recorded as in the case of that using no optical absorbent.

A thermal recording card prepared by heat laminating the thermal recording material containing an optical absorbent, before or after thermal recording, with a plastic film can be recorded with light through the laminated plastic film.

The bisurea compound of Formula (1) of the present invention is a color developer which is superior in color developing function and background color stability to heat and solvents. The reason for the superior background color stability of the bisurea compound of Formula (1) of the present invention has yet not to clarified. However, this is considered as follows:

The bisurea compound of Formula (1) has the phenolic hydroxyl group of the hydroxyarylureido structure and the urea structure of the hydroxyarylureido structure as positions which are considered to have a color developing function (function to develop the color of the dye precursor). However, of these positions, the urea structure is considered to participate mainly in the color developing function. Depending on the condition, the urea structure changes in structure as shown below. Since this change is a phenomenon similar to the keto/enol tautomerism, and is referred here to as keto-form and enol-form for convenience.

$$\underset{\text{Keto-form}}{-\text{NH}-\overset{\text{O}}{\underset{\|}{\text{C}}}-\text{NH}-} \longleftrightarrow \underset{\text{Enol-form}}{-\text{N}=\overset{\text{OH}}{\underset{|}{\text{C}}}-\text{NH}-}$$

It is considered that the urea structure must have the enol-form in order to function as a color developer. Since enol-formation requires a high temperature. Since the thermal head instantaneously provides a high temperature of 200° to 300° C., the urea compound contacting with the thermal head undergoes enol-formation to have a color developing function. Therefore, the urea compound does not change and maintains the keto-form until the enol-formation temperature is reached, and the background color remains unchanged. This would be the reason for the high heat resistance.

On the other hand, the phenolic hydroxyl group is considered to function as an acid catalyst for enol-formation of the urea structure, rather than participating in the color developing function. The phenolic hydroxyl group is considered to serve for reduction of the enol-formation temperature and improvement of an enol-formation rate (conversion rate from keto-form to enol-form). Therefore, the thermal recording material with improved recording sensitivity can be obtained.

The reason why the background color is not changed by writing with an oil ink is considered as due to the fact that the bisurea compound of the present invention is low in solubility in the solvents used in the oil ink, and the dye precursor and the color developer are not substantially mixed with each other even when contacting the solvents.

DETAILED DESCRIPTION OF EXAMPLES

Synthesis of bisurea compounds

Typical synthesis examples of the bisurea compound will be shown below. Other bisurea compounds have been synthesized according to the procedures of Synthesis Examples 1 to 10.

Synthesis Example 1 o-Aminophenol (12.0 g, 110 mM) was dissolved in ethyl acetate (400 ml). To the solution, a solution of hexamethylenediisocyanate (8.4 g, 50 mM) in ethyl acetate (100 ml) was added dropwise. After stirring at 50° C. for 1 hour, a white precipitate was generated. The precipitate was filtered, thoroughly washed with ethyl acetate, and n-hexane, until 1 spot was obtained on TLC (thin layer chromatograph) to obtain Compound A-3. (Yield: 81.7%) (Data of Compound A-3)

Melting point: 169° C.

$^1$H-NMR (solvent/DMSO-d6): 1.30 (4H, broad s), 1.41 (4H, broad S), 3.06 (4H, dd, J=12.0, 6.3), 6.64–6.81 (3H, m), 7.83(1H, s), 7.84 (1H, s), 7.85 (1H, s), 7.86 (1H, s), 9.81 (2H, broad s). IR (cm$^{-1}$): 3360, 2938, 2852, 1626, 1559.

Molecular weight determined by mass spectrum was 336.

Synthesis Example 2 m-Aminophenol (12.0 g, 110 mM) was dissolved in ethyl acetate (400 ml). To the solution, a solution of hexamethylenediisocyanate (8.4 g, 50 mM) in ethyl acetate (100 ml) was added dropwise. After stirring at 50° C. for 1 hour, a white precipitate was generated. The precipitate was filtered, thoroughly washed with ethyl acetate, and n-hexane, until 1 spot was obtained on TLC to obtain Compound A-4. (Yield: 83.1)

(Data of Compound A-4)

Melting point: 212° C.

$^1$H-NMR (solvent/DMSO-d6): 1.29 (4H, broad s), 1.41 (4H, broad s), 3.05 (4H, dd, J=12.0, 6.2), 6.01 (2H, broad s), 6.26 (2H, dd, J=8.0, 1.8), 6.68 (2H, broad d, J=8.0), 6.94 (2H, td, J=8.0, 1.8), 6.95 (2H, d, J=1.8), 8.21 (1H, s), 8.22 (1H, s), 9.14 (1H, s), 9.15 (1H, s).

IR (cm$^{-1}$): 3358, 2937, 2861, 1609, 1567.

Molecular weight determined by mass spectrum was 386.

Synthesis Example 3 p-Aminophenol (12.0 g, 110 mM) was dissolved in acetone (400 ml). To the solution, a solution of hexamethylenediisocyanate (8.4 g, 50 mM) in acetone (50 ml) was added dropwise. After stirring at 50° C. for 1 hour, a white precipitate was generated. The precipitate was filtered, thoroughly washed with acetone, and n-hexane, until 1 spot was obtained on TLC to obtain Compound A-5.

(Yield: 82.3%)

(Data of Compound A-5)

Melting point: 216°–217° C.

$^1$H-NMR (solvent/DMSO-d6): 1.28 (4H, broad s), 1.40 (4H, broad s), 3.05 (4H, collapsed d, J=6.5), 5.89 (2H, broad s), 6.60 (4H, d, J=8.2), 7.11 (4H, d, J=8.2), 7.96 (1H, s), 7.97 (1H, s), 8.84 (1H, s), 8.87 (1H, s).

IR (cm$^{-1}$): 3336, 2930, 2858, 1634, 1562.

Molecular weight determined by mass spectrum was 386.

Synthesis Example 4

4-Amino-o-cresol (13.5 g, 110 mM) was dissolved in acetone (200 ml). To the solution, a solution of hexamethylenedIisocyanate (8.4 g, 50 mM) in acetone (50 ml) was added dropwise. After stirring at 50° C. for 1 hour, a white precipitate was generated. The precipitate was filtered, thoroughly washed with acetone, and n-hexane, until 1 spot was obtained on TLC to obtain Compound A-12.

(Yield: 80.1%)

(Data of Compound A-12)

Melting point: 204°–205° C.

$^1$H-NMR (solvent/DMSO-d6): 1.28 (4H, broad s), 1.39 (4H, broad s), 2.06 (6H, s), 3.03 (4H, dd, J=12.0, 6.2), 6.09 (2H, t, J=4.4), 6.47 (2H, dd, J=8.5, 2.5), 6.53 (2H, d, J=2.5), 7.24 (2H, d, J=8.5), 7.31 (2H, s), 8.95 (2H, s).

IR (cm$^{-1}$): 3319, 2935, 2857, 1633, 1562.

Molecular weight determined by mass spectrum was 414.

Synthesis Example 5

3-Hydroxy-4-methoxyaniline (15.3 g, 110 mM) was dissolved in acetone (200 ml). To the solution, a solution of hexamethylenediisocyanate (8.4 g, 50 mM) in acetone (200 ml) was added dropwise. After stirring at 50° C. for 1 hour, a white precipitate was generated. The precipitate was filtered, thoroughly washed with acetone, and n-hexane, until 1 spot was obtained on TLC to obtain Compound A-16.

(Yield: 73.7%)

(Data of Compound A-16)

Melting point: 218° C.

$^1$H-NMR (solvent/DMSO-d6): 1.27 (4H, broad s), 1.39 (4H, broad s), 3.03 (4H, dd, J=12.0, 6.3), 5.92 (2H, t, J=5.5), 6.65 (2H, dd, J=8.6, 2.2), 6.72 (2H, d, J=8.6), 6.93 (2H, d, J=2.2), 8.05 (2H, s), 8.79 (2H, broad s).

IR (cm$^{-1}$): 3310, 2936, 2857, 1620, 1582.

Molecular weight determined by mass spectrum was 446.

Synthesis Example 6

4-Amino-2-nitrophenol (16.9 g, 110 mM) was dissolved in acetone (200 ml). To the solution, a solution of hexamethylenediisocyanate (8.4 g, 50 mM) in acetone (200 ml) was added dropwise. After stirring at 50° C. for 2 hours, a precipitate was generated. The precipitate was filtered, thoroughly washed with acetone, and n-hexane, until 1 spot was obtained on TLC to obtain Compound A-21. (Yield: 81.3%)

(Data of Compound A-21)

Melting point: 213° C.

$^1$H-NMR (solvent/DMSO-d6): 1.27 (4H, broad s), 1.41 (4H, broad s), 3.05 (4H, dd, J=12.5, 6.4), 6.14 (2H, t, J=5.5), 7.00 (2H, d, J=9.0), 7.39 (2H, dd, J=9.0, 2.6), 8.12 (2H, d, J=2.6), 8.51 (2H, s), 10.04 (2H, broad s).

IR (cm$^{-1}$): 3311, 2934, 2859, 1630, 1563.

Molecular weight determined by mass spectrum was 476.

Synthesis Example 7

2-Amino-4-chlorophenol (15.7 g, 110 mM) was dissolved in ethyl acetate (200 ml). To the solution, a solution of hexamethylenediisocyanate (8.4 g, 50 mM) in ethyl acetate (50 ml) was added dropwise. After stirring at 50° C. for 1.5 hour, a precipitate was generated. The precipitate was filtered, thoroughly washed with ethyl acetate, and n-hexane, until 1 spot was obtained on TLC to obtain Compound A-22. (Yield: 93.5)

(Data of Compound A-4)

Melting point: 206° C.

$^1$H-NMR (solvent/DMSO-d6): 1.30 (4H, broad s), 1.41 (4H, broad s), 3.06 (4H, dd, J=12.0, 6.5), 6.71 (2H, d, J=8.5), 6.72 (2H, dd, J=8.5), 6.75 (4H, d, J=8.5), 6.91 (2H, broad s), 7.96 (2H, s), 8.06 (1H, s), 8.07 (1H, s), 10.04 (2H, broad s).

IR (cm$^{-1}$): 3361, 2936, 2859, 1625, 1558.

Molecular weight determined by mass spectrum was 455.

Synthesis Example 8 p-Aminophenol (12.0 g, 110 mM) was dissolved in acetone (400 ml). To the solution, a solution of 4,4-diphenylmethanediisocyanate (12.5 g, 50 mM) in acetone (50 ml) was added dropwise. After stirring at 50° C. for 1 hour, a white precipitate was generated. The precipitate was filtered, thoroughly washed with acetone, and n-hexane, until 1 spot was obtained on TLC to obtain Compound A-25. (Yield: 70.7%)

(Data of Compound A-25)

Melting point; 300° C.

$^1$H-NMR (solvent/DMSO-d6): 3.79 (2H, s), 6.67 (4H, dd, J=7.0, 1.8), 7.09 (4H, d, J=8.4), 7.20 (4H, dd, J=7.0, 1.8), 7.33 (4H, d, J=8.4), 8.27 (2H, s), 8.44 (2H, s), 9.05 (2H, s).

IR (cm$^{-1}$): 3320, 1642, 1568.

Molecular weight determined by mass spectrum was 468.

Synthesis Example 9 p-Aminophenol (12.0 g, 110 mM) was dissolved in acetone (400 ml). To the solution, a solution of xylylenediisocyanate (9.4 g, 50 mM) in acetone (50 ml) was added dropwise. After stirring at 50° C. for 1 hour, a white precipitate was generated. The precipitate was filtered, thoroughly washed with acetone, and n-hexane, until 1 spot was obtained on TLC to obtain Compound A-72. (Yield: 76.1%)

(Data of Compound A-72)

Melting point: 234° C.

$^1$H-NMR (solvent/DMSO-d6): 4.24 (4H, d, J=6.0), 6.42 (2H, t, J=5.8), 6.62 (4H, dd, J=6.8, 2.0), 7.14 (4H, dd, J=6.8, 2.0), 7.10–7.30 (4H, m), 8.16 (2H, s), 8.93 (2H, s).

IR (cm$^{-1}$): 3332, 1638, 1566.

Molecular weight determined by mass spectrum was 406.

Synthesis Example 10

4-Amino-2,6-dichlorophenol (19.6 g, 110 mM) was dissolved in ethyl acetate (200 ml). To the solution, a solution of hexamethylenediisocyanate (8.4 g, 50 mM) in ethyl acetate (50 ml) was added. After stirring at 50° C. for 1.5 hour, a precipitate was generated. The precipitate was filtered, thoroughly washed with acetone, and n-hexane, until 1 spot was obtained on TLC to obtain Compound A-81. (Yield: 77.3%)

(Data of Compound A-81

Melting point: 200° C.

$^1$H-NMR (solvent/DMSO-d6): 1.26 (4H, broad s), 1.40 (4H, broad s), 3.17 (4H, dd, J=12.0, 6.0), 6.16 (2H, broad s), 7.38 (4H, s), 8.40 (2H, s), 10.05 (2H, s).

IR (cm$^{-1}$): 3328, 2937, 2859, 1635, 1580.

Molecular weight determined by mass spectrum was 524.

<Production of thermal recording material>

In the following description, part and % indicate part by weight and % by weight, respectively.

EXAMPLES 1–35

As shown below, thermal recording materials were produced using the bisurea compound of the present invention and either of the six types of dye precursors shown below (Table 1, Table 2).

ODB: 3-diethylamino-6-methyl-7-anilinofluorane
ODB-2: 3-dibutylamino-6-methyl-7-anilinofluorane
TH-107: 3-dibutylamino-7-(o-chloroanilino)fluorane
CVL: 3,3-bis(p-dimethylaminophenyl)-6-dimethylaminophthalide
New Blue: 3-(4-diethylamino-2-ethoxyphenyl)-3-(1-ethyl-2-methylindol-3-yl)-4-azaphthalide
Indolyl Red: 3,3-bis(1-ethyl-2-methylindol-3-yl)phthalide Specifically, a color developer dispersion (Liquid A) and a dye precursor dispersion (Liquid B) of the following compositions were milled by a sand grinder to an average particle diameter of 1 micron.

| (Liquid A: color developer dispersion) | |
|---|---|
| Bisurea compound of the present invention | 6.0 parts |
| 10% Aqueous polyvinylalcohol solution | 18.8 |
| Water | 11.2 |
| (Liquid B: dye precursor dispersion) | |
| Each dye precursor | 2.0 parts |
| 10% Aqueous polyvinylalcohol solution | 4.6 |
| Water | 2.6 |

Then, the Liquid A (color developer dispersion), the Liquid B (dye precursor dispersion), and a kaolin clay dispersion were mixed in the following ratio to obtain a coating color.

| Liquid A: color developer dispersion | 36.0 parts |
|---|---|
| Liquid B: dye precursor dispersion | 9.2 |

| Kaolin clay (50% dispersion) | 12.0 |

The coating color was coated on one side of a 50 g/m² base paper to a coating amount of 6.0 g/m², dried, and supercalendered to a smoothness of 500 to 600 seconds to obtain a thermal recording material.

Comparative Examples 1–7

Thermal recording materials for comparative tests were prepared using the compounds shown below as color developers and using the same procedure as in Examples 1–35. (Table 3) (Color developer compounds)
Bisphenol A (B-1)
Bisphenol S (B-2)
4-Hydroxy-4'-iso-propoxydiphenylsulfone (B-3)
4-Hydroxy-4'-n-butyroxydiphenylsulfone (B-4)
Phenylurea (B-5) described in Japanese OPI 58-211496
Bisurea compound (B-6) described in Japanese OPI 05-147357
1-p-Toluyl-3-phenylurea (B-7)

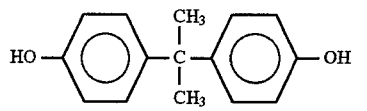
(B-1)

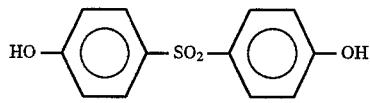
(B-2)

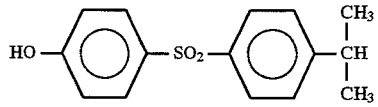
(B-3)

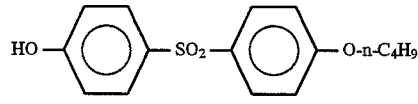
(B-4)

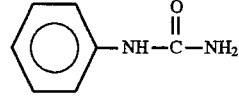
(B-5)

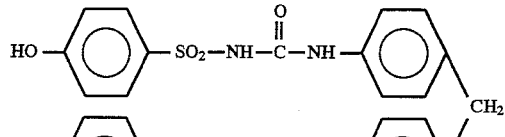
(B-6)

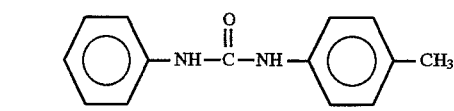
(B-7)

Specifically, dispersions of the above individual color developer compounds of the following composition were milled by a sand grinder to an average particle diameter of 1 micron.

| (Liquid C: color developer dispersion) | |
|---|---|
| Color developer compound (B-1 to B-7) | 6.0 parts |
| 10% Aqueous polyvinylalcohol solution | 18.8 |
| Water | 11.2 |

Then, Liquid C (color developer dispersion), the ODB dispersion (Liquid B) used in Examples 1–23, and a kaolin clay dispersion were mixed in the following ratio to obtain a coating color.

| Liquid C: color developer dispersion | 36.0 parts |
|---|---|
| Liquid B: dye precursor dispersion | 9.2 |
| Kaolin clay (50% dispersion) | 12.0 |

The coating color was coated on one side of a 50g/m² base paper to a coating amount of 6.0 g/m² and dried, and the sheet was supercalendered to a smoothness of 500 to 600 seconds to obtain a comparative sample of thermal recording material.

Evaluation of thermal recording materials

The resulting thermal recording materials were tested by a recordability test using a word processor printer, a thermal stability test, and an oil ink adaptability test.

Recordability test:

To evaluate the recording adaptability, the thermal recording material was recorded using a word processor printer (RUPO-JW95G: Toshiba) at a maximum energy, and the recorded portion was measured by a Macbeth densitometer (RD-914, an amber filter used. Hereinafter density was measured in this condition). In this case, the greater the Macbeth value, the higher the recording density and the better the recording adaptability (recording sensitivity).

Thermal stability test:

To evaluate the thermal stability of background color of the thermal recording material, the recording material was pressed against a hot plate heated individually at 90° C., 120°, and 135° C. at a pressure of 10 g/cm² for 5 seconds, and the treated material was measured by a Macbeth densitometer. In this case, the smaller the Macbeth value, the better the thermal resistance of background color of the thermal recording material.

Oil ink adaptability test (discoloration of background color by oil ink):

The recording material was written with a felt pen of red oil ink (Magic INK No. 500: Teranishi Kagaku), and visually measured for a degree of discoloration compared to the original color of the red ink.

A: No discoloration
B: Little discoloration
C: Slight discoloration
D: Considerable discoloration The evaluation results of the thermal recording materials of Examples 1–35 and Comparative Examples 1–7 are shown in Tables 1 to 3.

TABLE 1

| Entry | Color developer | Dye | Background color before recording | Recorda-bility test | Thermal resistance test 90° C. | 120° C. | 135° C. | Oil ink adapta-bility |
|---|---|---|---|---|---|---|---|---|
| Ex. 1 | Comp. A3 | ODB | 0.04 | 1.41 | 0.05 | 0.12 | 0.18 | A |
| Ex. 2 | Comp. A4 | ODB | 0.05 | 1.35 | 0.05 | 0.06 | 0.07 | A |
| Ex. 3 | Comp. A5 | ODB | 0.04 | 1.28 | 0.04 | 0.05 | 0.06 | A |
| Ex. 4 | Comp. A9 | ODB | 0.03 | 1.19 | 0.04 | 0.05 | 0.07 | A |
| Ex. 5 | Comp. A12 | ODB | 0.04 | 1.17 | 0.05 | 0.07 | 0.08 | A |
| Ex. 6 | Comp. A16 | ODB | 0.06 | 1.19 | 0.06 | 0.08 | 0.09 | A |
| Ex. 7 | Comp. A21 | ODB | 0.06 | 1.37 | 0.06 | 0.09 | 0.12 | A |
| Ex. 8 | Comp. A22 | ODB | 0.04 | 1.32 | 0.04 | 0.11 | 0.22 | A |
| Ex. 9 | Comp. A25 | ODB | 0.04 | 1.05 | 0.04 | 0.07 | 0.09 | A |
| Ex. 10 | Comp. A26 | ODB | 0.05 | 1.00 | 0.06 | 0.08 | 0.10 | A |
| Ex. 11 | Comp. A37 | ODB | 0.04 | 1.06 | 0.06 | 0.08 | 0.09 | A |
| Ex. 12 | Comp. A39 | ODB | 0.05 | 0.98 | 0.06 | 0.07 | 0.10 | A |
| Ex. 13 | Comp. A41 | ODB | 0.05 | 0.95 | 0.06 | 0.08 | 0.11 | A |
| Ex. 14 | Comp. A42 | ODB | 0.04 | 0.96 | 0.06 | 0.08 | 0.09 | A |
| Ex. 15 | Comp. A44 | ODB | 0.03 | 0.96 | 0.05 | 0.06 | 0.08 | A |
| Ex. 16 | Comp. A51 | ODB | 0.05 | 0.92 | 0.06 | 0.08 | 0.10 | A |
| Ex. 17 | Comp. A52 | ODB | 0.06 | 0.93 | 0.07 | 0.09 | 0.11 | A |
| Ex. 18 | Comp. A53 | ODB | 0.04 | 0.91 | 0.05 | 0.06 | 0.09 | A |

TABLE 2

| Entry | Color developer | Dye | Background color before recording | Recorda-bility test | Thermal resistance test 90° C. | 120° C. | 135° C. | Oil ink adapta-bility |
|---|---|---|---|---|---|---|---|---|
| Ex. 19 | Comp. A55 | ODB | 0.06 | 1.15 | 0.06 | 0.11 | 0.15 | A |
| Ex. 20 | Comp. A63 | ODB | 0.04 | 1.03 | 0.04 | 0.05 | 0.05 | A |
| Ex. 21 | Comp. A66 | ODB | 0.03 | 1.11 | 0.03 | 0.06 | 0.08 | A |
| Ex. 22 | Comp. A72 | ODB | 0.04 | 1.12 | 0.04 | 0.05 | 0.07 | A |
| Ex. 23 | Comp. A81 | ODB | 0.05 | 1.16 | 0.05 | 0.06 | 0.08 | A |
| Ex. 24 | Comp. A3 | CVL | 0.05 | 1.09 | 0.05 | 0.05 | 0.06 | A |
| Ex. 25 | Comp. A4 | CVL | 0.05 | 1.07 | 0.05 | 0.05 | 0.05 | A |
| Ex. 26 | Comp. A5 | CVL | 0.05 | 1.08 | 0.05 | 0.05 | 0.05 | A |
| Ex. 27 | Comp. A4 | ODB-2 | 0.03 | 1.38 | 0.03 | 0.05 | 0.07 | A |
| Ex. 28 | Comp. A5 | ODB-2 | 0.03 | 1.30 | 0.03 | 0.05 | 0.07 | A |
| Ex. 29 | Comp. A4 | TH-107 | 0.03 | 1.33 | 0.03 | 0.03 | 0.03 | A |
| Ex. 30 | Comp. A5 | TH-107 | 0.03 | 1.31 | 0.03 | 0.03 | 0.03 | A |
| Ex. 31 | Comp. A4 | New Blue | 0.06 | 1.10 | 0.06 | 0.08 | 0.10 | A |
| Ex. 32 | Comp. A5 | New Blue | 0.07 | 1.04 | 0.06 | 0.08 | 0.09 | A |
| Ex. 33 | Comp. A25 | New Blue | 0.06 | 1.01 | 0.06 | 0.07 | 0.08 | A |
| Ex. 34 | Comp. A4 | Indolyl Red | 0.04 | 0.88 | 0.06 | 0.07 | 0.09 | A |
| Ex. 35 | Comp A5 | Indolyl Red | 0.06 | 0.89 | 0.06 | 0.07 | 0.08 | A |

TABLE 3

| Entry | Color developer | Dye | Background color before recording | Recorda-bility test | Thermal resistance test 90° C. | 120° C. | 135° C. | Oil ink adapta-bility |
|---|---|---|---|---|---|---|---|---|
| Comp. Ex. 1 | B1 | ODB | 0.06 | 1.44 | 0.21 | 1.51 | 1.52 | D |
| Comp. Ex. 2 | B2 | ODB | 0.06 | 1.30 | 0.08 | 0.21 | 0.48 | D |
| Comp. Ex. 3 | B3 | ODB | 0.04 | 1.50 | 0.13 | 1.55 | 1.55 | D |
| Comp. Ex. 4 | B4 | ODB | 0.04 | 1.52 | 0.04 | 0.13 | 0.90 | D |
| Comp. Ex. 5 | B5 | ODB | 0.03 | 1.28 | 0.03 | 0.06 | 0.41 | A |
| Comp. Ex. 6 | B6 | ODB | 0.06 | 1.14 | 0.07 | 0.11 | 0.92 | A |
| Comp. Ex. 7 | B7 | ODB | 0.05 | 1.55 | 0.13 | 0.55 | 1.08 | A |

EXAMPLE 36

The thermal recording materials of Example 2 and Example 3. were subjected to a thermal resistance test at 150° C. (using the hot plate heated to 150° C. in the above-described thermal resistance test), and the treated recording materials were measured for Macbeth density of the background color portion, which were 0.11 and 0.08, respectively.

EXAMPLE 37

The thermal recording material of Example 2 was put between pouch films and heat laminated using a simple lamination apparatus (MS Pouch H-140: Meiko Shokai). The recording portion and the background color portion were measured by a Macbeth densitometer. The recording portion had a density of 1.23 and that of the background color portion was 0.12.

EXAMPLE 38

The thermal recording material of Example 3 was put between pouch films and heat laminated using a simple lamination apparatus (MS Pouch H-140: Meiko Shokai). The recording portion and the background color portion were measured by a Macbeth densitometer. The recording portion had a density of 1.20 and that of the background color portion was 0.10.

EXAMPLE 39

The thermal recording material of Example 9 was put between pouch films and heat laminated using a simple lamination apparatus (MS Pouch H-140: Meiko Shokai). The recording portion and the background color portion were measured by a Macbeth densitometer. The recording portion had a density of 1.10 and that of the background color portion was 0.12.

EXAMPLE 40

The thermal recording material of Example 22 was put between pouch films and heat laminated using a simple lamination apparatus (MS Pouch H-140: Meiko Shokai). The recording portion and the background color portion were measured by a Macbeth densitometer. The recording portion had a density of 1.14 and that of the background color portion was 0.11.

EXAMPLE 41

The thermal recording material of Example 23 was put between pouch films and heat laminated using a simple lamination apparatus (MS Pouch H-140:Meiko Shokai). The recording portion and the background color portion were measured by a Macbeth densitometer. The recording portion had a density of 1.21 and that of the background color portion was 0.13.

EXAMPLE 42

The thermal recording material of Example 1 was toner recorded by a copier (NP6060: CANON). Satisfactory recording was achieved with no change in the background color.

EXAMPLE 43

The thermal recording material of Example 2 was toner recorded by a copier (NP6060: CANON). Satisfactory recording was achieved with no change in the background color.

EXAMPLE 44

The thermal recording material of Example 3 was toner recorded by a copier (NP6060: CANON). Satisfactory recording was achieved with no change in the background color.

EXAMPLE 45

The thermal recording material of Example 8 was toner recorded by a copier (NP6080: CANON). Satisfactory recording was achieved with no change in the background color.

EXAMPLE 46

The thermal recording material of Example 12 was toner recorded by a copier (NP6060: CANON). Satisfactory recording was achieved with no change in the background color.

EXAMPLE 47

The thermal recording material of Example 22 was toner recorded by a copier (NP6060: CANON). Satisfactory recording was achieved with no change in the background color.

<Production of thermal recording material containing an optical absorbent>

EXAMPLES 48–52

As shown below, optical recording materials were produced using ODB as a dye precursor, Compound A-3 as a color developer, and a heat melt of the following absorbent dyes and a sensitizer as an optical absorbent.

Cyanine type dye (NK-2015: Nippon Kanko Shikiso)

Naphthalocyanine type dye (NIR-14: Yamamoto Kasei)

Immonium type dye (IRG-002; Nippon Kayaku)

Anthraquinone type dye (IR-750: Nippon Kayaku)

Bisdithiobenzylnickel complex (BDBNi)

Specifically, 94 parts of 4-biphenyl-p-tolylether was mixed with 6 parts of an optical absorbent, heated to 100° to 150° C. to melt, and then crushed to obtain an optical absorbent. An optical absorbent dispersion of the following composition was milled by a sand grinder to an average particle diameter of 1 micron.

| (Liquid D: Optical absorbent dispersion) | |
|---|---|
| Optical absorbent | 4.0 parts |
| 10% Aqueous Polyvinylalcohol solution | 10.0 |
| Water | 6.0 |

Then, the dispersion of Compound A-3 (Liquid A), the ODB dispersion (Liquid B), Liquid C (optical absorbent dispersion), and a kaolin clay dispersion used in Example 3 were mixed in the following ratio to obtain a coating color.

| Liquid A (color developer dispersion) | 36.0 parts |
|---|---|
| Liquid B (dye precursor dispersion) | 9.2 |
| Liquid E (optical absorbent dispersion) | 20.0 |
| Kaolin clay (50% dispersion) | 12.0 |

The coating color was coated on one side of a 50 g/m$^2$ base paper in a coating amount of 6.0 g/m$^2$ and dried, and the sheet was supercalendered to a smoothness of 500 to 600 seconds to obtain a thermal recording material.

EXAMPLES 53–54

Thermal recording materials were produced using an absorbent dye alone in place of the heat melt of the individual dye and a sensitizer.

Toluenedithiolnickel complex (TDNi)

1,1,5,5-Tetrakis(p-diethylaminophenyl)-3-methoxy-1,4-pentadiene (TDEPMP)

The optical absorbent color developer dispersion (Liquid E) of the following composition was milled by a sand grinder to an average particle diameter of 1 micron.

| (Liquid E: Optical absorbent color developer dispersion | |
|---|---|
| Compound A-2 of Example 2 | 6.0 parts |
| TDNi or TDEPMP | 1.0 |
| 10% Aqueous Polyvinylalcohol solution | 10.0 |
| Water | 3.96 |

Then, the optical absorbent color developer dispersion (Liquid E), the ODB dispersion (Liquid B), and a kaolin clay dispersion were mixed in the following ratio to obtain a coating color.

| Liquid E (optical absorbent color developer) | 36.0 parts |
|---|---|
| Liquid B (dye precursor dispersion) | 9.2 |
| Kaolin clay (50% dispersion) | 12.0 |

The coating color was coated on one side of a 50 g/m$^2$ base paper in a coating amount of 6.0 g/m$^2$ and dried, and the sheet was supercalendered to a Smoothness, of 500 to 600 seconds to obtain a thermal recording material.

<Evaluation of thermal recording materials containing optical absorbent>

The resulting thermal recording materials were subjected to a recordability test.

Recordability test (optical recording):

Using a laser plotter described in Japanese OPI 03-239598, the optical recording material was irradiated with a laser light, and the recorded portion was measured by a Macbeth densitometer. Using a 30 mW semiconductor laser LT015MD (SHARP) with an oscillation wavelength of 830 nm as a recording light sources, an aspheric plastic lens AP4545 (Konica) with a numerical aperture of 0.45 and a focal length of 4.5 mm as an optical converging lens, a recording speed of 50 mm/sec, and a recording interval of 50 microns, a 1-cm square overall recording was obtained. The evaluation results are shown in Table 4.

TABLE 4

| Entry | Optical absorbent | Background color before recording | Optical recording test |
|---|---|---|---|
| Example 48 | NK-2015 | 0.12 | 1.35 |
| Example 49 | NTR-14 | 0.13 | 1.34 |
| Example 50 | IRG-002 | 0.14 | 1.39 |
| Example 51 | IR-075 | 0.13 | 1.29 |
| Example 52 | BDBNi | 0.15 | 1.28 |
| Example 53 | TDNi | 0.13 | 1.28 |
| Example 54 | TDEPMP | 0.12 | 1.31 |

The thermal recording materials of Examples 53 and 54 were subjected to a thermal resistance test (at 135° C.), the background color portion of the individual materials were measured. The results were 0.14 and 0.14, respectively.

The bisurea compound of the present invention is an epoch-making color developer that can provide a recording with a sufficient image density by a thermal head or the like while the background color portion is stable at environmental temperatures of 120° to 135° C.

Therefore, the present invention has the following effects.

(1) The thermal recording material of the present invention is superior in background color stability such as thermal resistance and solvent resistance compared with conventional thermal recording materials.

(2) The thermal recording material of the present invention can be used under severe conditions (e.g. at temperatures of 90°–135° C.) at which conventional products could not be used.

(3) The thermal recording material of the present invention can be freely written on the recording surface (surface having the thermal recording layer) with an oil ink.

(4) The thermal recording material of the present invention can be simply heat laminated by a simple laminator or the like. For example, cards and the like can be easily prepared.

(5) The thermal recording material of the present invention can be toner recorded.

The thermal recording material of the present invention can also be incorporated with an optical absorbent for use as an optical recording material having similar effects.

What is claimed is:

1. A thermal recording material having a thermal recording layer containing a colorless or pale colored dye precursor and a color developer reactable with said dye precursor upon heating to develop a color of said dye precursor, wherein said color developer is a bisurea compound of the following Formula (1),

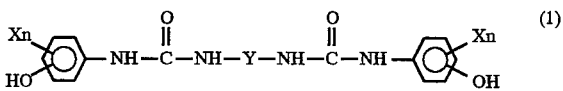

wherein

X denotes an alkyl group of 1 to 12 carbon atoms, a halogenated alkyl group of 1 to 6 carbon atoms, an alkoxy group of 1 to 6 carbon atoms, nitro group, halogen atom, or hydrogen atom;

Y denotes a divalent group of within 30 carbon atoms;

n is an integer of 1 or 2; and said thermal recording layer contains at least one of said bisurea compounds of Formula (1).

2. A thermal recording material having a thermal recording layer containing a colorless or pale colored dye precursor and a color developer reactable with said dye precursor upon heating to develop a color of said dye precursor, wherein said color developer is a bisurea compound of the following Formula (2),

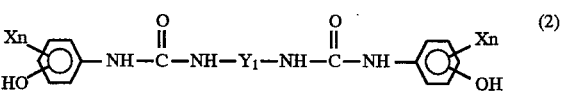

wherein

X denotes an alkyl group of 1 to 12 carbon atoms, a halogenated alkyl group of 1 to 6 carbon atoms, an alkoxy group of 1 to 6 carbon atoms, nitro group, halogen atom, or hydrogen atom;

$Y_1$ denotes a straight-chain alkylene group of 1 to 12 carbon atoms, or an alkylene group having a branched chain of 1 to 15 carbon atoms;

n is an integer of 1 or 2; and said thermal recording layer contains at least one of said bisurea compounds of Formula (2).

3. A thermal recording material having a thermal recording layer containing a colorless or pale colored dye precursor and a color developer reactable with said dye precursor upon heating to develop a color of said dye precursor, wherein said color developer is a bisurea compound of the following Formula (3),

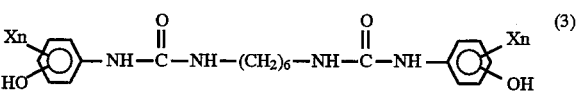

wherein

X denotes an alkyl group of 1 to 12 carbon atoms, an alkoxy group of 1 to 6 carbon atoms, nitro group, halogen atom, or hydrogen atom;

n is an integer of 1 or 2; and said thermal recording layer contains at least one of said bisurea compounds of Formula (3).

4. The thermal recording material of claim 1, claim 2, or claim 3, wherein the thermal recording layer contains an optical absorbent for converting absorbed light to heat.

5. The thermal recording material of claim 1, claim 2, or claim 3 laminated with a plastic film.

* * * * *